US010827857B2

(12) United States Patent
Lewis

(10) Patent No.: US 10,827,857 B2
(45) Date of Patent: Nov. 10, 2020

(54) MIST GENERATOR FOR STERILIZING FORCED AIR SYSTEMS

(71) Applicant: Randall J Lewis, Bethesda, MD (US)

(72) Inventor: Randall J Lewis, Bethesda, MD (US)

(*) Notice: Subject to any disclaimer, the term of this patent is extended or adjusted under 35 U.S.C. 154(b) by 0 days.

(21) Appl. No.: 16/841,387

(22) Filed: Apr. 6, 2020

(65) Prior Publication Data

US 2020/0245790 A1    Aug. 6, 2020

Related U.S. Application Data

(63) Continuation-in-part of application No. 15/722,822, filed on Oct. 2, 2017, which is a continuation-in-part (Continued)

(51) Int. Cl.
| | | |
|---|---|---|
| *A61F 7/00* | (2006.01) | |
| *A47G 9/02* | (2006.01) | |
| *A61L 2/04* | (2006.01) | |

(52) U.S. Cl.
CPC .......... *A47G 9/0215* (2013.01); *A61F 7/0085* (2013.01); *A61F 7/0097* (2013.01); (Continued)

(58) Field of Classification Search
CPC ... A47G 9/0215; A61F 7/0097; A61F 7/0085; A61F 2007/0054; A61L 2/04; A61L 2202/24
See application file for complete search history.

(56) References Cited

U.S. PATENT DOCUMENTS

| 1,121,227 A | 12/1914 | Mitchell |
|---|---|---|
| 2,259,712 A | 10/1941 | Sweetland |
| (Continued) | | |

FOREIGN PATENT DOCUMENTS

| CA | 3016038 A1 | 9/2017 | |
|---|---|---|---|
| WO | WO-2007069922 A1 * | 6/2007 | ............... A61B 5/01 |
| WO | WO2017151556 A1 | 9/2017 | |

*Primary Examiner* — Kaitlyn E Smith
*Assistant Examiner* — Yasamin Ekrami
(74) *Attorney, Agent, or Firm* — Ernest D. Buff & Associates, LLC; Ernest D. Buff

(57) ABSTRACT

A mist generator improves the sterility of blowers having controlled forced air systems. In one embodiment, the mist generator has a chamber adapted to receive a disinfectant adapted for attachment to an output opening of a blower for delivery into the chamber of forced air carrying misted disinfectant. The main body also includes an output duct or aperture adapted for attachment to a second hose which, in turn, is adapted for attachment to an inlet opening of the blower for delivery of disinfectant misted air through internal components of the blower. Alternatively, there is used a disinfectant filter formed as a sterilizing grid having a screen coated with a soft porous surface material impregnated with a liquid disinfectant. The soft porous surface material releases said liquid disinfectant when forced air moves through the filter. In both embodiments, sterile water is introduced to take up residual disinfectant and the vapor captured in a dry filter or desiccant material and removed from the system. The mist generator improves the sterility of the blower to mitigate microbial contamination of forced air delivery systems.

13 Claims, 15 Drawing Sheets

Related U.S. Application Data of application No. 15/334,507, filed on Oct. 26, 2016, now Pat. No. 9,901,483, which is a continuation-in-part of application No. 15/056,120, filed on Feb. 29, 2016, now Pat. No. 9,504,601.

(52) U.S. Cl.
CPC ......... *A61L 2/04* (2013.01); *A61F 2007/0054* (2013.01); *A61L 2202/24* (2013.01)

(56) References Cited

U.S. PATENT DOCUMENTS

| | | | |
|---|---|---|---|
| 2,504,308 A | 4/1950 | Donkle | |
| 2,753,435 A | 7/1956 | Jepson | |
| 2,978,225 A | 4/1961 | Dallas | |
| 4,094,357 A | 6/1978 | Sgroi | |
| 4,132,262 A | 1/1979 | Wibell | |
| 4,777,802 A | 10/1988 | Feher | |
| 4,884,304 A | 12/1989 | Elkins | |
| 5,015,442 A | 5/1991 | Hirai | |
| 5,225,167 A | 7/1993 | Wetzel | |
| 5,318,568 A | 6/1994 | Kaufmann | |
| 5,417,729 A | 5/1995 | Greenleaf, Sr. | |
| 5,523,057 A | 6/1996 | Mazzilli | |
| 5,902,413 A | 5/1999 | Puszko | |
| 5,968,084 A | 10/1999 | Augustine et al. | |
| 6,036,738 A * | 3/2000 | Shanbrom | B01D 46/0028 55/524 |
| 6,508,989 B1 | 1/2003 | Urrustiet et al. | |
| 7,114,204 B2 | 10/2006 | Patrick | |
| 7,837,721 B2 | 11/2010 | Augustine et al. | |
| 8,066,947 B2 | 11/2011 | Niazi | |
| 8,414,671 B2 | 4/2013 | Augustine et al. | |
| 9,504,601 B1 | 11/2016 | Lewis | |
| 9,901,483 B2 | 2/2018 | Lewis | |
| 2002/0058974 A1 | 5/2002 | Van Duren | |
| 2003/0216660 A1 | 1/2003 | Ben-Oren | |
| 2003/0208251 A1 | 11/2003 | Papay | |
| 2006/0076507 A1 | 4/2006 | Avnery | |
| 2010/0234794 A1 | 9/2010 | Weadock | |
| 2015/0129439 A1 | 5/2015 | Frieson | |
| 2015/0182650 A1* | 7/2015 | Leight | A61L 2/24 422/292 |
| 2018/0028702 A1 | 2/2018 | Lewis | |

* cited by examiner

MIST GENERATOR FOR STERILIZING FORCED AIR SYSTEMS

CROSS-REFERENCE TO RELATED APPLICATIONS

This application is a continuation-in-part of applicant's U.S. patent application Ser. No. 15/722,822, filed Oct. 2, 2017 which, in turn, is a continuation-in-part of applicant's U.S. patent application Ser. No. 15/334,507, filed Oct. 26, 2016, now U.S. Pat. No. 9,901,483 which, in turn, is a continuation-in-part of U.S. patent application Ser. No. 15/056,120, filed Feb. 29, 2016, now U.S. Pat. No. 9,504,601, the disclosures of which are hereby incorporated in their entirety by reference thereto.

1. Field of the Invention

The present invention relates to improvements in sterility of forced air systems; and, more particularly, to an antimicrobial mist generator utilized with systems employing forced air, heated air or cooled air, such as hospital equipment, health care equipment, commercial and/or residential forced air systems, for facilitating and/or maintaining sterility.

2. Description of the Prior Art

Numerous prior art patents and disclosures relate to warming of a patient mattress or blanket by the passage of warmed fluids. Warmed fluids may be heated water or heated air. If a fluid-filled device leaks or ruptures, the heated water disadvantageously creates puddles of leaked water around the patient and on the operating room floor. Water filled blankets are heavy, and the patient may find these blankets highly uncomfortable. Mattresses and blankets that circulate warm air discharge the air through a plurality of exit passages in the form of high velocity jets. Because the internal conduits of the blower are not sterile, the air discharged from the device may contain microbes. The discharge also creates turbulent circulation currents in the room air that may pick up microbes in floor dust and deliver them to the patient's operative area, as well as hospital room workers.

U.S. Pat. No. 1,121,277 to Mitchell discloses a warming appliance for beds. This warming apparatus circulates warm water. The disclosure of this patent shows the bed having a plurality of pipes through which heated water is circulated. A hot water heater or boiler is connected to a pipe that feeds the bed heating pipes. Warm air is not circulated through the bed.

U.S. Pat. No. 2,259,712 to Sweetland discloses a bed warmer apparatus. A fan blows air through an electric heater and the warmed air is passed through a pipe in the bed. The bed warmer requires power to drive the blower motor. A flexible hose conveys warm air to the cushion, which serves the double purpose of supporting the bed cover and providing warmth in the bed. A conventional type of bed cover is used. The blower passes air over electrical heaters to warm the air, which is passed through pipes in the bed. The interior of the blower is not sterilized. The warm air is not returned to the blower since this is not a closed system. Release of the warm air can cause currents of unsterile air, containing bacteria, to surround the patient or the operative site, increasing prospects for infections.

U.S. Pat. No. 2,504,308 to Donkle discloses a heating and cooling cover. The bed has a heating or cooling cover supplied with working fluid from a refrigerator or a heat pump. The cover does not employ warm air. A working fluid is returned to the refrigeration or heat pump system through a heat exchanger, which heats or cools the area adjacent to the refrigeration or heat pump unit.

U.S. Pat. No. 2,753,435 to Jepson discloses a thermal blanket. The thermal blanket is on a bed and is provided with a fluid circulating unit. The fluid circulating unit is provided with a knob to adjust the temperature of the thermal blanket. The fluid is indicated to be distilled water. The device disclosed by the Jepson patent does not circulate warm air within the blanket.

U.S. Pat. No. 2,978,225 to Dallas discloses a thermal blanket. The thermal blanket is provided with tubes through which liquid is circulated. The thermal blanket has a plurality of fluid passageways disposed in a parallel relationship. The edge includes a liquid distribution manifold unit. The thermal blanket does not circulate warm air to provide warmth to the patient.

U.S. Pat. No. 4,094,357 to Sgroi discloses a heat transfer blanket. The heat transfer blanket has a plurality of flexible sheath heat pipes that provide a uniform heating or cooling pattern therein. The ends of the flexible heat pipes that are free from the blanket are thermally coupled to a combination heating and cooling system. When utilizing the heating system, the flexible heat pipes provide elevated temperatures at the blanket surfaces. When utilizing the cooling system, the flexible heat pipes provide lower than ambient temperatures at the blanket surfaces. A solid metallic rod is affixed to one end of the pipe. A wick extends the entire length of the interior of the pipe, which is partially filled with a liquid that becomes a vapor upon sufficient heating. The end of the pipe in which liquid is situated accepts heat from the surrounding area, causing the liquid to vaporize. The vapor ultimately communicates with the other end of the pipe. At this end, cooling effects are introduced, and the vapor condenses back to a liquid state. Liquid then travels along the wick to the end of a tube containing the liquid. The efficiency of thermal coupling between opposite ends of the heat pipe is substantially higher than the coupling efficiency of an equivalent diameter and length of a solid copper rod. The heat transfer means for warming or cooling the blanket is by evaporation heating or cooling of liquid contained in the wick. Warm air is not passed within pipes in the heat transfer blanket.

U.S. Pat. No. 4,132,262 to Wibell discloses a heating and cooling blanket. This cooling and heating blanket has a blanket enclosure with heating means including a plurality of flexible elements positioned within the enclosure for being electrically energized to supply heat to the enclosure so that the enclosure may be retained above room temperature. A cooling means includes a plurality of flexible fluid carrying conduits positioned within the enclosure through which a heat transfer fluid can flow, such that the enclosure may be retained below room temperature. Control means including an electric motor and a pump driven thereby are located remotely relative to the enclosure. A flexible conduit means connects the enclosure and the cooling means. A regulating means is operatively associated with the heating means and the cooling means. The regulating means is adapted to energize the control means or the heating means in response to increases and decreases of the temperature associated with the enclosure. With this arrangement, the temperature of the blanket may be retained above or below the room temperature in which the blanket is located. The heating and cooling means are separate from each other. The heating means comprises electrical heating wires, which are heated by the passage of an electrical current. Heating of the blanket is not achieved by the passage of warm air.

U.S. Pat. No. 4,777,802 to Feher discloses a blanket assembly and selectively adjustable apparatus for providing heated or cooled air thereto. This blanket assembly has an outer layer constructed of a relatively close-weave fabric preventing airflow therethrough. Underneath the top layer is a second layer of material edge connected to the top layer and which is constructed of a material permeable to air, such as relatively thin taffeta, for example. A cavity between the two layers receives pressurized cooled or heated air that passes through the air-permeable layer to cool or heat the individual using the blanket assembly. A modified blanket assembly construction includes rigid edge wall members holding the outer and inner layers separated at a predetermined spacing. This reduces "pinch-off" between the layers that would restrict airflow within parts of the cavity or chamber. Peltier effect elements are selectively energizable to heat or cool air provided to the blanket assembly cavity. The heating/cooling of the patient bed is effected by a closed circuit with a solid-state PN junction to create the heating/cooling based on the Peltier effect. Passage of direct current in one direction causes one PN junction to heat while the other junction cools. The heated PN junction supplies heat to warm the patient bed while the coolness of the other junction is discharged in air surrounding the patient as well as the operating room. The device disclosed by the Feher patent does not use circulation of warm air in a closed system to warm the bed of a patient, and there is no sterilization of the internal portion of the system, creating the possibility of infecting the patient and workers in the operating room.

U.S. Pat. No. 4,884,304 to Elkins discloses a bedding system with selective heating and cooling. This bedding system has provision for heating or cooling a person and for applying the heating or cooling only in areas of the bed where the person is located. A sealed three-ply heat transfer and insulating device covers the mattress, below the contour sheet or other covering which comes in contact with the person's body. A wicking contour sheet or other cover capable of absorbing any condensation on the surface of the three-ply device may optionally be used. Between the lower two plies of the three-ply material is channeled a flow of coolant liquid at a regulated temperature that is close to human skin temperature. Above these two plies. i.e., between the middle ply and the upper ply, is a sealed envelope containing slightly pressurized air. A lightweight, well-insulated comforter is also recommended to isolate the sleeper from the thermal ambient environment. The bedding system includes a temperature control unit and a mattress cover device, which is positioned over a mattress. The mattress cover device includes liquid flow channels and preferably a gas envelope or plenum space located above the liquid flow channels. The multiplicity of liquid flow channels is interconnected to form one or more circulation paths. The mattress is heated by liquid flow channels. It is not heated by the passage of warm air.

U.S. Pat. No. 5,968,084 to Augustine et al. discloses a thermal blanket. This thermal blanket includes an inflatable covering with a head end, a foot end, two edges and an undersurface. The covering is inflated through an inlet at the foot end by a thermally controlled inflating medium. An aperture array on the undersurface of the covering exhausts the thermally controlled inflating medium from the covering. Exhaust port openings are provided at the edges of the covering to vent the inflating medium, which enhances circulation of the thermally controlled medium through the cover. An uninflatable section is provided at the head end, together with an absorbent bib attached to the covering, adjacent the uninflatable section. An uninflatable section may also be provided at the foot end, having a pair of seams to form an erectable drape section. When inflated, the device self-erects and provides a bath of thermally controlled inflating medium to the interior of the erected structure. The enhanced circulation of the medium through the covers maintains a relatively high average temperature under the blanket and a relatively uniform distribution of temperature in the inflating medium, which is exhausted through the apertures into the structure's interior. When the structure covers a patient, the uninflatable section at the head end provides a relatively unobstructed view of the patient's face, while the absorbent bib maintains a relatively sanitary environment in the area beneath the patient's head. The uninflatable section at the foot end retains heat from the inflating medium to warm the patient's feet and insulate the bare skin of the feet from excessive conductive heat from the hose connected to the inflation inlet. The thermal blanket may be sized to cover selected areas of a patient, such as the upper body, including the chest, arms, or shoulders, or the lower body, including the pelvic and groin area and the legs. The warmed air is exhausted underside of the thermal blanket through the apertures provided. The flow of warm air through the apertures occurs at high velocity, thus bringing microbes and dust to the patient by the turbulent movement of ambient airflow.

U.S. Pat. No. 7,114,204 to Patrick discloses a method and apparatus for transferring patients. This patient transfer apparatus includes an inflatable mattress, alternatively with a rigid top board with a patient restraint system on which a patient can be placed, when patient immobilization is required. A portable cart is included with a chamber for storage of a plurality of mattresses.

U.S. Pat. No. 7,837,721 to Augustine, et al. discloses a patient comfort apparatus and system. This apparatus and system thermally comfort a patient; and includes a clinical garment such as a hospital gown, robe, bib, and other equivalents provided with pneumatic, convective thermal treatment for persons or animals. The pneumatic convective device provides convective warming focused or directed primarily on the thorax or body core. The pneumatic convective device includes at least one inlet accessed through a clinical garment, a region in distribution with the inlet for distributing a stream of pressurized, thermally treated air, and a permeable member for emitting pressurized, thermally treated air from the distribution region. As shown in FIG. 1A, the sheets 114 and 116 form between themselves a pneumatic structure to receive and distribute pressurized air within itself. At least one permeable member of the device (the sheet 114, for example) cooperates with the pneumatic structure to emit pressurized air from the device. In this regard, one end of an air hose may be received through an inlet port 127. A stream of pressurized, thermally conditioned air introduced through the air hose fills the space between the sheets 114 and 116 and is distributed throughout the space. The pressurized air is emitted from the pneumatic structure through the air-permeable sheet 114. Motion of the emitted air supports heat transfer with a body adjacent, next to or near the pneumatic structure facing the permeable sheet 114. The permeable sheet has holes that deliver the pressurized warm air at high velocity, producing turbulent airflow adjacent to the patient, bringing dust and microbes to the patient U.S. Pat. No. 8,414,671 to Augustine, et al. discloses personal air filtration devices for use with bedding structures. These devices, methods, and systems create a zone of filtered air proximate a patient's head. They include an air filtration device having a blower configured to be disposed within, below, or affixed to a bedding structure; an air plenum in flow communication with the blower and in support of the head of the user and having an air delivery surface configured to distribute the air flow to the zone of filtered air; and a filter disposed within the device for filtering the air flow before it is distributed to the zone of filtered air. Filtered air is exhausted, surrounding the patient, and producing airflow that is turbulent and can deliver microbes and dust to the patient. There is no sterilization of the interior of the blower, as recommended by the FDA.

U.S. Pat. No. 5,225,167 to Wetzel discloses a room air sterilizer mounts on the wall of the room and traps airborne particulate in a HEPA filter. An ultraviolet germicidal lamp destroys any biocontamination on the trapped particulates. The sterilizer has an elongated vertical housing with a return air grille near or at its lower end and a HEPA filter assembly disposed at an outflow port at its upper end. The HEPA filter is preferably a quarter cylinder, and the sterilizer lamp is situated to expose the inner or intake side of the filter to the sterilizing ultraviolet radiation. A prefilter can be situated ahead of the blowers for the sterilizer and can have an associated ultraviolet sterilizer lamp.

U.S. Pat. No. 5,015,442 to Hirai discloses a sterilizing/deodorizing apparatus having a fan for creating airflow in one direction in a box-like body. The body has divided air passages, one of the air passages having an ozonizer and an air-permeable ozone-decomposing catalyzer, and the other air passage simply allowing untreated air to flow therethrough.

U.S. Pat. No. 5,417,729 to Greenleaf discloses a modular air cleaning system having at least one filter module having a closed plenum box provided with male and female air flow porting structure, one of which porting structure provides an air inlet, and the other of which provides an air outlet, each of the porting structures is in substantially cylindrical form, and projects outwardly from the box and each has a section of substantially the same diameter lying adjacent the box, a shoulder on each of the sections peripherally circumscribing the same at a short distance outwardly from the box and adapted to engage end portions of a flexible hose for preventing its withdrawal from the sections, the male porting structure having a reduced diameter segment lying outwardly of the adjacent section and adapted to telescope within the female porting structure of another plenum box, and an annular seal within the female porting structure adapted to engage the segment and form a substantially gas-tight seal there against.

U.S. Pat. No. 5,523,057 to Mazzilli discloses a filtration system for use in residential and commercial buildings. The filtration apparatus consists of a galvanized steel for support of a tactified filter followed by a 254 nm ultraviolet light with the sterilized air then passed through an activated carbon filter for removal of chemical vapors. The filtration apparatus works in conjunction with a remotely located power supply pack, which includes an air pressure activator to allow operation of the ultraviolet lights only when air movement is detected in a ventilation system. Installation of the device is compact, allowing placement in residential locations in conventional heater and air conditioning systems.

U.S. Pat. No. 6,508,989 to Urrusti, et al. discloses an air sterilization system for child incubators to provide the child with air which is less polluted or free from pathogenic microorganisms that might put its health at risk or prolong its stay in the incubator and/or clinic or hospital, and that of the other persons or patients that might come into contact with the air exiting the same incubator in the case of a child with an infectious manifestation.

U.S. Pat. No. 8,066,947 to Niazi discloses an air scrubber for eliminating associated airborne contaminants and sterilizing air provided to protect against nosocomial infections, environmental allergens, weapons of biological and chemical attacks, and operations requiring a clean environment. The air scrubber includes a housing containing an alkali solution at pH 14 through which air passes and suspended liquid particles removed; provides are made for use in central air-conditioning systems, stand-alone applications, and portable use along with respirators.

U.S. Pat. App. Pub. No. 20060076507 to Avnery discloses a system for sterilizing air, including an air duct for flowing the air therethrough. A first electron beam generator is positioned relative to the duct for irradiating the air flowing therethrough with a first electron beam. The first electron beam disables biological substances within the air.

It has been found that sterilization of forced-air blowers utilized for warming blankets and mattresses is necessary and has been specifically recommended by the FDA. Standards being implemented require frequent cleaning and sterility owing to findings that contaminated forced air can increase the concentration of contaminated airborne particles over a surgical site. Despite the finding that forced-air blowers need regular maintenance and cleaning, the current cleaning method typically involves simply wiping down the blower device. Wipe-down of the blower frequently fails to clean the inside of the blower itself, and therefore forced-air from the blower typically poses contamination threats to the surgical site when the forced-air blower is being used with patient warmers or lifters.

Based on the foregoing, there exists a need in the art for improved sterility of the internal components of non-closed circuit forced hot air warmers/blowers, thereby mitigating and/or preventing infections of patients when the blower is being utilized, as well as decreasing exposure of contaminants of operating room hospital workers and occupants of commercial and residential buildings.

SUMMARY OF THE INVENTION

The present invention provides a system for an antimicrobial mist generator for use as a stand-alone internal sterilizer for closed circuit and open circuit forced hot air devices that deliver heated air with improved sterility. An antimicrobial mist generator is in-line with a forced-air blower to sequentially circulate antiseptic solution, water, and clean-air within the internal components of the forced air system, forming a closed system during the process. The antimicrobial mist generator may be employed in a closed system device or in a non-closed system device that is temporarily adapted to connect to the mist generator for disinfection. The mist generator is first partially filled with a liquid disinfectant, which is taken up by the forced air circulating through the chamber and delivered into the internal components of the blower to clean and sterilize the components. Once the chamber is dry, water is placed in the chamber and is taken up by the circulating air, which becomes saturated with water vapor. The residual disinfectant in the system is dissolved into the water vapor circulating in the saturated air. A desiccant or other dry material is then placed in the chamber. The water vapor and dissolved residual disinfectant are taken up in the dry material. When the cycle is complete, the chamber is disconnected and discarded, the air lines reconnected, and air can then be circulated through an internally sterile system. After use of the antimicrobial chamber, this sanitation of the internal components prevents unsterile air currents containing microbes from being delivered from the blower when it is in-line with a patient warmer, lifter or other machine, thereby decreasing the risk of infection from blower contaminants.

The mist generator delivers an antimicrobial or disinfectant through a blower and/or blower system in order to sterilize the blower and/or blower system and decrease the possibility of exposure to infecting microbes. It is intended to perform internal sterilization of the blower and/or blower system, including the blower, blower vents, internal blower components, air vents, and hoses. The present invention relates to improvements in the sterility of forced air systems employing forced air, heated air and/or cooled air, including, for non-limiting example, hospital machines/health care equipment, /portable oxygen machines/commercial and/or residential forced air systems for facilitating and/or maintaining internal sterility. Hospital machines/health care equipment contemplated include respirators, anesthesia machines, and the like. Commercial and/or residential forced air systems include a full range of blower/forced air devices for use with heaters, coolers, and air blowers, such as those used in commercial and/or residential forced air systems, as well as forced air systems, such as air conditioners and the like, used in land vehicles, including trucks, automobiles, trailers and tractors. These systems may include heating or cooling systems for residential and commercial buildings (hospitals, high-rise, or otherwise involving units sharing forced air system components or vents), transportation vehicles (cruise ships, boats, trains, airplanes, and the like). Savings in reduced material and production costs, as well as weight reduction and improved sterility, represent improvements in maintaining sterilization of these blower systems.

In a first embodiment, the mist generator for improved sterility of blowers having controlled forced air comprises a main body having a top wall with an opening, the opening traversing into a chamber adapted to receive a disinfectant, sidewalls and a bottom wall. An inlet duct is provided that is adapted for attachment to a first hose which, in turn, is adapted for attachment to an output opening of the blower for delivery of forced air into the chamber to carry misted air. An output duct is adapted for attachment to a second hose which, in turn, is adapted for attachment to a blower inlet opening of the blower for delivery of disinfectant misted air, water, and clean air through internal components of the blower. The mist generator improves the sterility of the blower to mitigate microbial contamination of forced air delivery systems.

Another aspect of the invention provides a mist generator for improved sterility of blowers having controlled forced air delivery, comprising a disinfectant filter formed as a sterilizing grid having a screen coated with a soft porous surface material impregnated with a liquid disinfectant, wherein said disinfectant is released from the soft porous surface into the air passing through the filter. When the filter is dry, it can be removed and impregnated with clean or sterile water. The filter is reinserted, and the air flowing through the system takes up the water. This can be repeated, or another separate filter, moistened with water, may be used. This water again dissolves the residual disinfectant within the system. The water, including the contained disinfectant, is removed by inserting a dry filter and allowing the circulating water to be taken up by the dry filter, which is removed and discarded. The mist generator cycle improves the sterility of the blower to mitigate microbial contamination of forced air delivery systems.

BRIEF DESCRIPTION OF THE DRAWING

The invention will be more fully understood and further advantages will become apparent when reference is had to the following detailed description of the preferred embodiments of the invention and the accompanying drawing, in which:

FIG. 9b illustrates another embodiment of a spray capsule/cartridge adapted to be inserted within the mist generator of FIG. 9a;

FIG. 9c illustrates an embodiment of a capsule/cartridge adapted to be inserted within the mist generator of FIG. 9a;

FIG. 9d illustrates another embodiment of a capsule/cartridge adapted to be inserted within the mist generator of FIG. 9a;

DETAILED DESCRIPTION OF THE INVENTION

Figure 1:
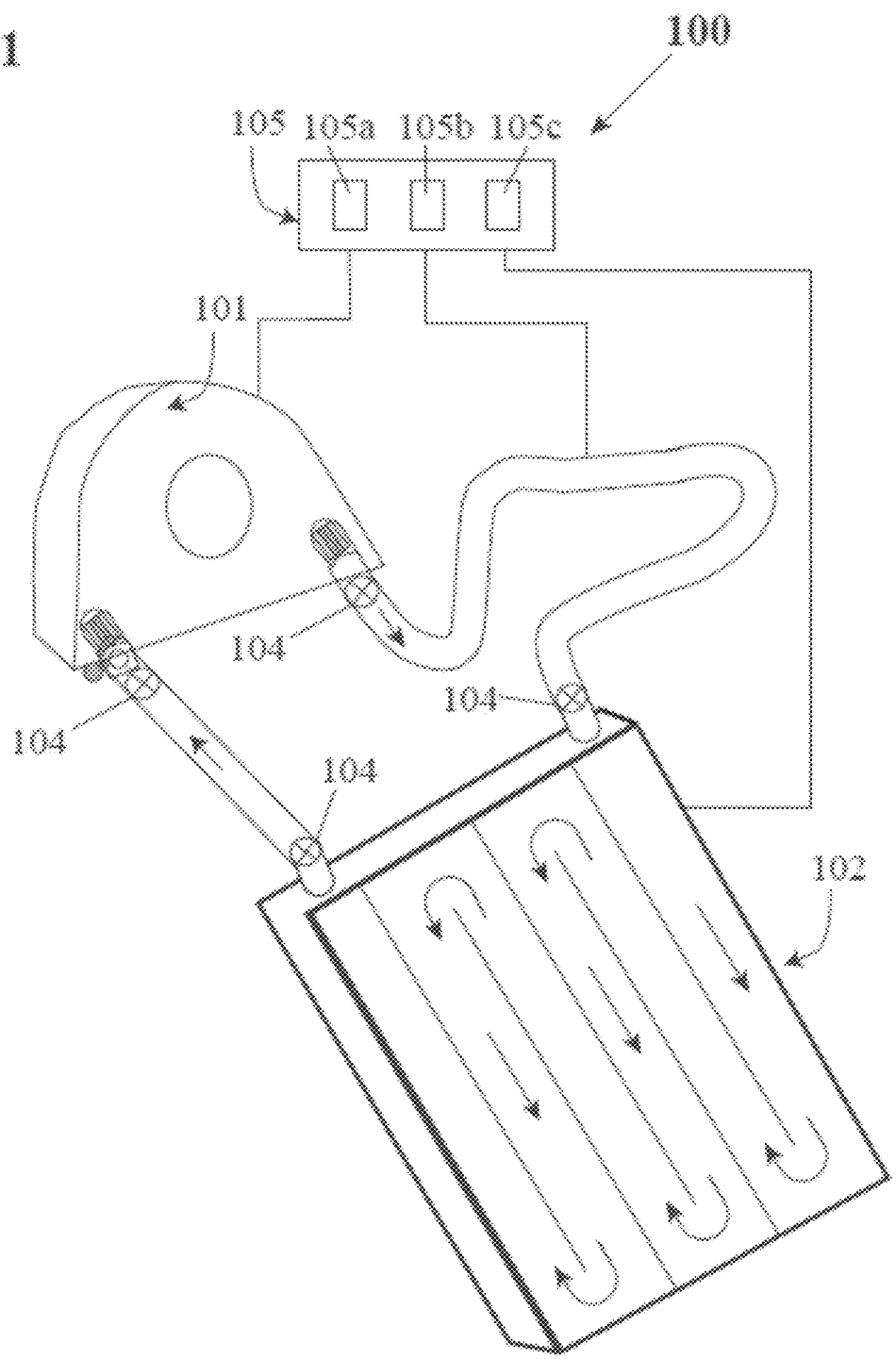
FIG. 1 illustrates an embodiment of a system for delivering warm air to patient beds and blankets in a closed circulating circuit.

The objective of the invention is to provide a mist generator for delivering an antimicrobial or disinfectant mist to a blower and/or blower system in order to sterilize the blower and/or blower system and decrease the possibility of exposure to infecting microbes. The subject mist generator is intended to perform internal sterilization of the blower and/or blower system, including the blower, blower vents, internal blower components, air vents, and hoses. The present invention relates to improvements in the sterility of forced air systems employing forced air, heated air and/or cooled air, including, for non-limiting example, hospital machines/health care equipment, portable oxygen generators/commercial and/or residential forced air systems for facilitating and/or maintaining internal sterility. Hospital machines/health care equipment contemplated include respirators, anesthesia machines, and the like. Commercial and/or residential force air system uses include a full range of blower/forced air devices for use with heaters, coolers, and air blowers, such as those used in commercial and/or residential forced air systems, as well as forced air systems, such as air conditioners and the like, used in land vehicles, including trucks, automobiles, trailers and tractors. These systems may include heating or cooling systems for residential and commercial buildings (hospitals, high-rise, or otherwise involving units sharing forced air system components or vents), transportation vehicles (cruise ships, boats, trains, airplanes, and the like). Most have removable and/or disposable filters which help to remove dust particles from the airflow but do not sterilize or disinfect the interior of the machines. Savings in reduced material and production costs, as well as weight reduction and improved sterility represent improvements in maintaining sterilization of these blower systems.

In one aspect, the subject chamber is appointed to be used with open circuit heating/cooling devices, including for example commercial and/or residential forced air systems and/or aircraft, cruise ship and/or train forced air systems, to create the temporarily closed circuit during sanitization of these devices. Generally, in one aspect, the mist generator includes a chamber having an input connected via a hose to an air output of a blower of a system to be sanitized, and an output connected to an end of the return via a hose connected to an air intake/undersurface of the blower. Liquid disinfectant/water is placed in the chamber up to a fill line located at a level under the input and output of the mist generator's chamber. As hot air from the blower blows into the chamber, disinfecting mist is generated and is blown into the air intake of the blower to sanitize the internal components within the blower. A connection port is provided for attachment of the hose from the chamber to fit over and preferably substantially completely cover the blower air input or return vent/port. The connection port preferably includes a rim with an adhesive located thereon for adhesive, temporary attachment to the blower air input port/vent. If there are multiple return ports in the system, only one return remains open. Coverage of any return port may also be achieved with a sheet of plastic wrap, held over the port by its inherent adherence and the slight suction generated by the airflow. After the mist stage is finalized and the liquid evaporated, dry desiccant and/or a hygroscopic absorbent substance is inserted into the chamber, and air continues to run so that any remaining moisture in the closed-circuit system is absorbed by the desiccant. After sterilization is complete, the mist generator is disconnected from the forced air device, and the device is reconnected to its operation configuration. The subject mist generator and its contents may be disposable. Alternatively, the mist generator may be reusable.

Temporary conversion to a closed circuit is implemented as the subject mist generator/antimicrobial chamber is used to sterilize heating/cooling/air circulation device internal structures and hoses with disinfectant vapor. In another aspect of the invention, a disinfectant filter or sponge is inserted into the main system with all but one outlet closed. The disposable filter or sponge is shaped to fit into a filter slot of the forced air system. When dry, the filter/sponge is removed and saturated with water or another moist sponge/filter is inserted. The system is again run and the disinfectant is taken up in the water vapor. Finally, a dry filter/sponge is inserted, and the system is run "dry" to capture moisture in the filter or chamber with desiccant therein. Lastly, all outlets of the system are opened. The convenience associated with insertion of the disinfectant filter or sponge and its ready replacement with a dry filter/sponge commend this aspect of the invention for use in forced air systems, such as air conditioners and the like, used in land vehicles, including trucks, automobiles, trailers, tractors, aircraft, cruise ships and trains.

In yet another aspect of the invention, the subject mist generator for delivering an antimicrobial or disinfectant mist is utilized for hospital equipment or health care equipment that implements a forced air unit or blower, such as for non-limiting example, intraoperative patient warmers and/or patient lifters, respirators, anesthesia machines, forced air chambers, isolation chambers, and the like, for internal sterilization. Usage for patient warmers, intraoperative mattresses, hospital ventilators, anesthesia machines, portable oxygen machines (O2 concentrators) carried by patients, and/or oxygen supply systems in order to sterilize the blower for later use, thereby decreasing the possibility of patients suffering infections and hospital workers in the operating room being exposed to infecting microbes. The subject mist generator is intended to perform internal sterilization of the blower and hoses of medical devices.

The generator must be used in a closed circuit, although that may be only temporary. Disinfectant or antimicrobial is introduced into the chamber and vaporized by warm air circulated by the blower. After the disinfectant sterilizes the inside surfaces of the blower and hoses, an aliquot of water is introduced into the chamber and is similarly vaporized, taking up the disinfectant residue. A dry desiccant is then appointed to be introduced into the chamber and absorbs the mist. After the mist is absorbed and the system is clean and dry, the blower is then turned off. The mist generator is removed from the system and discarded, if it is disposable; or, if not disposable, is simply emptied.

The subject antimicrobial or disinfectant mist generator is operable as a stand-alone internal sterilizer for non-closed-circuit hot forced air devices or blowers, including medical devices, commercial and/or residential devices, and devices for transportation. Internal sterilization of the blowers is effectuated through use of the antimicrobial mist generator to mitigate virus and/or infection risks caused by contaminated airflow of the forced air device or blower. The system both disinfects the interior of the device and recaptures the disinfectant, so that disinfectant vapor is not blown out of the machine and people are not subjected to inhaling chemical vapors.

An outflow/output duct of the antimicrobial mist generator is attached to a flexible hose that connects to an air inflow duct of any non-closed circuit device, temporarily making it run as a closed circuit and allowing internal sterilization, including drying, without releasing disinfectant vapor into the environment. The antimicrobial mist generator is preferably, but not necessarily, disposable; and achieves the internal sterilization that is currently impossible with patient heating devices now in use. Concerning medical equipment, the FDA has recommended "regular cleaning" of patient heating devices; therefore, the subject antimicrobial mist generator provides an add-on stand-alone internal sterilizer for ready compliance with FDA recommendations. In one embodiment, the antimicrobial mist generator avoids a port into its chamber that could be opened for filling and instead is constructed to have a soft diaphragm through which fluids are introduced with a needle and syringe, similar to medicine vials, in order to avoid contamination. Desiccant is then introduced into the chamber via a removable port.

The term non-closed circuit or open circuit refers generally to blowers having an outlet air duct for delivering forced air to a blower system implemented in hospital equipment, commercial and/or residential forced air systems, and/or transportation forced air systems, and an air inlet duct for pulling air from the atmosphere into the blower and no return of warm air to the blower. As used herein, the term closed-circuit refers generally to a pathway wherein there is a closed loop with no waste outlet or perforation of the blanket with all air returned via a separate duct to the blower.

Concerning medical equipment, for example, measurements have shown that a surgical patient under anesthesia loses about 1.6 degrees C. body temperature during the first hour. Such body temperature loss can lead to hypothermia, shivering, and may compromise the patient's healing ability. [See http://solutions.3m.com/wps/portal/3M/en_EU/Healthcare-Europe/EU-Home/Products/InfectionPrevention/Patient_Warming/.] Patient warming beds and warming blankets are essential to prevent this onset of patient hypothermia. For the past two decades, maintenance of patient body temperature during surgery has largely been achieved with forced hot air warming; this process replaced circulating hot water blankets, which were cumbersome and often ruptured, covering the floor with water. Tent, blanket, and mattress designs have also been used. Virtually all of these have been inexpensive and disposable, and have attempted to avoid the problem of difficult and often incomplete cleaning between uses. All of the currently used forced hot air devices have a blanket or pad with multiple holes that emit the warmed air around the patient or an open tent over the patient into which the warm air is blown. Some recent studies have documented that the release or leakage of the forced air causes unwanted air currents that bring up potentially unclean air from near the floor or cause increased numbers of particles and bacteria to circulate over the prepped area of the surgical incision, increasing the risk of operative infection. Examination has also revealed bacteria collecting within the blowers. Another study demonstrated that air currents interfere with the laminar airflow, sometimes used in the operating room to discourage bacterial contamination. The FDA has also recently released an alert, describing their concerns and the need for a regular program of cleaning and maintenance of heater/cooler devices. While the contention that these devices are related to an increase in operative infections has been questioned, it seems reasonable to attempt to avoid air leakage and any possibly undesirable air currents that might increase infection risk. Avoiding the buildup of bacteria within the blower is obviously a reasonable goal. Bacterial contamination related to increased infection has recently been reported in the liquid of water blankets. Staying with a forced hot air system that employs inexpensive, disposable mattresses, and blankets that do not need to be cleaned is clearly desirable.

Recently FDC has issued the following warning located at http://www.medscape.com/viewarticle/852750 which is reproduced below:

FDA Warns Infections a Risk With Heater-Cooler Devices

Megan Brooks

Disclosures|Oct. 15, 2015

The use of heater-cooler devices has been associated with nontuberculous mycobacterium (NTM) infections, primarily in patients undergoing cardiothoracic surgeries, the US Food and Drug Administration (FDA) warned today.

Heater-cooler devices are used during medical and surgical procedures to warm or cool a patient, as appropriate. The devices include water tanks that provide temperature-controlled water to external heat exchangers or warming/cooling blankets through closed circuits.

Although the water in the circuits does not come into direct contact with the patient, there is the potential for contaminated water to enter other parts of the device or transmit bacteria through the air, via the device's exhaust vent, into the environment and to the patient, the FDA notes in a safety communication posted on its website. Between January 2010 and August 2015, the FDA received 32 reports of patient infections associated with heater-cooler devices or bacterial heater-cooler device contamination, with 25 reported this year.

"Some reports describe NTM infections related to cardiothoracic surgeries, but other reports do not specify the procedure the patient was undergoing," the FDA notes. Eight reports were related to three events describing patient infections occurring in US healthcare facilities, whereas the other 24 reports involved facilities outside the United States, mostly in Western Europe.

In some cases, patients presented with infections several months to years after their surgical procedure. The FDA is not aware of NTM infections acquired by hospital staff.

The FDA says it is "actively" monitoring the situation and will provide updates as appropriate.

The aim of today's safety communication is to "heighten awareness about infections associated with heater-cooler devices and steps health care providers and health facilities can take to mitigate risks to patients," they say.

Recommendations

In addition to following standard precautions, the FDA recommends that healthcare facilities and staff using heater-cooler devices consider implementing the following measures to reduce risk to patients:

Strictly adhere to the cleaning and disinfection instructions provided in the manufacturer's device labeling. Ensure you have the most current version of the manufacturers' instructions for use readily available to promote adherence.

Do not use tap water to rinse, fill, refill, or top-off water tanks, as this may introduce NTM organisms. Use only sterile water or water that has been passed through a filter of less than or equal to 0.22 microns. When making ice needed for patient cooling during surgical procedures, use only sterile water or water that has been passed through a filter of less than or equal to 0.22 microns. Deionized water and sterile water created through reverse osmosis is not recommended because it may promote corrosion of the metal components of the system.

Direct the heater-cooler's vent exhaust away from the surgical field to mitigate the risk of aerosolizing heater-cooler tank water into the sterile field and exposing the patient.

Establish regular cleaning, disinfection, and maintenance schedules for heater-cooler devices according to the manufacturers' instructions to minimize the risk for bacterial growth and subsequent patient infection.

Develop and follow a comprehensive quality control program for maintenance, cleaning, and disinfection of heater-cooler devices. Your program may include written procedures for monitoring adherence to the program and documenting set up, cleaning, and disinfection processes before and after use.

Immediately remove from service heater-cooler devices that show discoloration or cloudiness in the fluid lines/circuits, which may indicate bacterial growth. Consult your hospital infection control officials to perform the appropriate follow-up measures and report events of device contamination to the manufacturer.

Consider performing environmental, air, and water sampling and monitoring if heater-cooler contamination is suspected. Environmental monitoring requires specialized expertise and equipment to collect and process samples, which may not be feasible in all facilities.

Healthcare facilities should follow their internal procedures for notifying and culturing patients if they suspect infection associated with heater-cooler devices.

Aspects of the present invention address the aforementioned issues by providing an antimicrobial mist generator operable as a stand-alone internal sterilizer for closed and non-closed-circuit blowers. Internal sterilization of the blower through use of the antimicrobial mist generator mitigates infection risks caused by contaminated airflow of the patient blower when it is being used with patient lifters and/or warmer devices. An outflow chamber/output duct of the antimicrobial mist generator is attached to a flexible hose that connects to an air inflow of any non-closed circuit device, temporarily making it run as a closed circuit and allowing internal sterilization, including drying, without releasing disinfectant vapor into the hospital environment. The antimicrobial mist generator, presumably, but not necessarily disposable, achieves the internal sterilization that is currently impossible with the patient heating devices now in use.

When the antimicrobial mist generator is in-line with a patient warming device circulating heated controlled warm air, the warm air passes through the antimicrobial mist generator and becomes substantially saturated by evaporated disinfectant forming an aerated mist. As warm air carrying sterilizing mist passes through the non-closed circuit patient warmer device the disinfectant kills harmful bacteria and germs so that the non-closed circuit patient warmer device's internal chambers are substantially free of bacteria and germs, thereby decreasing infection risks. Non-closed circuit patient warmer devices include, for non-limiting example, sterilized blowers with microprocessor-controlled air heating capabilities.

The disinfectant utilized has high volatility so that it is capable of evaporating and forming a saturated misted airflow upon application of the warm air pressure, yet substantially evaporating and dissipating to internally sterilize the non-closed circuit patient warmer device. The warming system circulates all of the warmed air within a closed circuit to provide internal sterilization, so that any air ultimately released outside the non-closed warm air circulating system is sterilized. Preferably, the disinfectant is a volatile liquid component that is adapted to vaporize as forced air blows over said disinfectant. Volatile liquid components preferably include alcohol-based solutions, containing one or more of isopropyl alcohol, ethanol (ethyl alcohol), and n-propanol solutions containing 60% to 95% alcohol. Non-alcohol based solutions may contain benzalkonium chloride or triclosan. Alternatively, the disinfectant may be a volatile liquid component saturated within a porous substrate, such as a sponge, capsule, cartridge or filter, and said liquid vaporizes and escapes the substrate as forced air blows over said substrate. The disinfectant may be in an aqueous solution with an alcohol solution or antiseptic therein.

The mist generator may include a transducer facilitating formation of the disinfectant mist, such as a piezoelectric transducer device including a transmitter, receiver, or sensor, for converting high-frequency electronic signals into high-frequency mechanical vibration. The disinfectant (typically aqueous solution) cavitates into vapor, which is forced through the surface of the disinfectant as a very fine mist, which is easily absorbed into the airflow. See, for example, http://www.piezo-ultrasonic.com/piezoelectric-transducer-applications-a006.html.

The closed circuit of the warming system is sterilized with an antimicrobial disinfectant spray or atomized mist. The warm air contained in the closed circulating system is sterile. At the end of use of the bed or blanket, the system can be sterilized with antimicrobial disinfectant atomized mist if desired and the disposable bed or blanket discarded.

The closed-circuit forced hot air warmer consists of a blower connected by flexible conduit using quick connect or other couplings to a terminal device, which may be a blanket or a mattress that is not an open tent. The air that enters the terminal device may pass through a HEPA filter with a pore size less than 0.22 microns to catch any bacteria or particles in the incoming airflow. The warm air passes through a structured chamber, or a folded tube within the chamber, so that the blanket or mattress is filled with warm air that passes slowly through the device to an outflow port and returns back to the blower in a completely closed system. There are no apertures to release warm air and no air leaks from the system, avoiding possible turbulence and air currents in the operating room. The internal chamber structure ensures that warm air is not shunted to the outflow port, but rather fills the entire chamber, so that the entire device remains warm, transmitting heat to the patient by direct contact and maintaining body temperature. The return air conduit is detachable from the device, as well. The blanket or mattress, therefore, remains a simple, inexpensive device and is suitable for disposal after use.

HEPA filters, if present, at the inflow and outflow portals of the blower, and the fact that each disposable pad is clean, help to avoid bacterial contamination. The unique design of the system makes sterilization of the air channels in the blower and the connecting tubes easy to perform. The detached ends of the flexible inflow and outflow lines are each connected to a small (detachable) chamber. A measured amount of liquid disinfectant is introduced through a separate port, and the blower is turned on. The circulating air will take up the disinfectant, which will be carried through the system as an aerosol. After a brief period, all internal surfaces are disinfected. A second aliquot of STERILE distilled water can be added later to rinse out the system. Following the two steps, a desiccant, paper, or sponge is introduced, and the blower again turned on. Any residual liquid is caught in the dry material. The two conduits are then disconnected, the chamber discarded or emptied, and the sterilized system is ready for use.

A port, which may have a filter, allows ambient air to enter the blower at the beginning of a cycle. When the system has been filled, and air begins to return via the outflow conduit, the entry portal closes automatically or is capped, and only air from the outflow conduit can enter the blower for recirculation.

FIG. 1 illustrates at 100 a system for delivering warm air to patient beds and blankets in a closed circulating circuit. The closed-circuit warm air delivery system comprises a blower 101 with microprocessor-controlled temperature, pressure, and flow control that has input and output ports which may be guarded by HEPA filters. The blower output port is connected to the input port of patient bed or blanket 102 using by flexible tubing with quick release connectors 104. The output port of the patient bed or blanket is connected to the input port of the blower 101 using flexible tubing again with quick release connectors 104. The microprocessor control panel is shown at 105. The microprocessor controls the warm air temperature at 105*a* warm airflow rate at 105*b* and warm air pressure at 105*c*. The warm airflow path is, therefore, a continuous closed circuit with no warm air escape location. The airflow rate is proportional to the speed of rotation of the blower motor. The electrical current supplied to the heating elements controls the warm air temperature.

Figure 2:
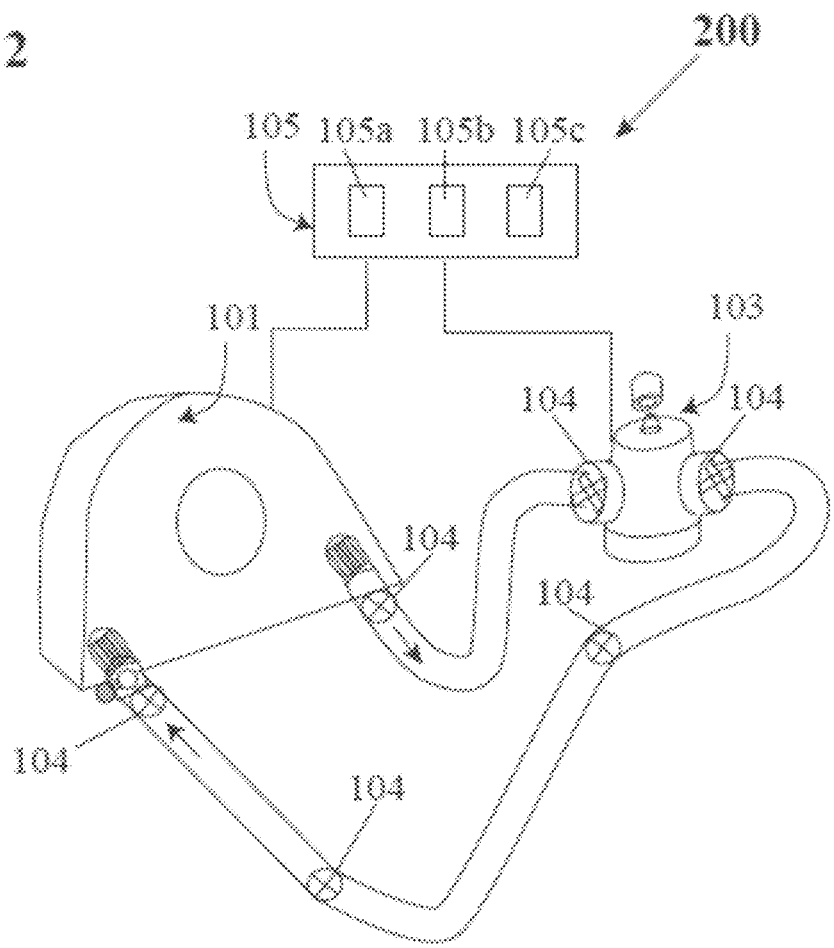
FIG. 2 illustrates an embodiment of the blower with air warmer machinery and flexible tubes being sterilized by the antimicrobial mist generator.
Figure 3:
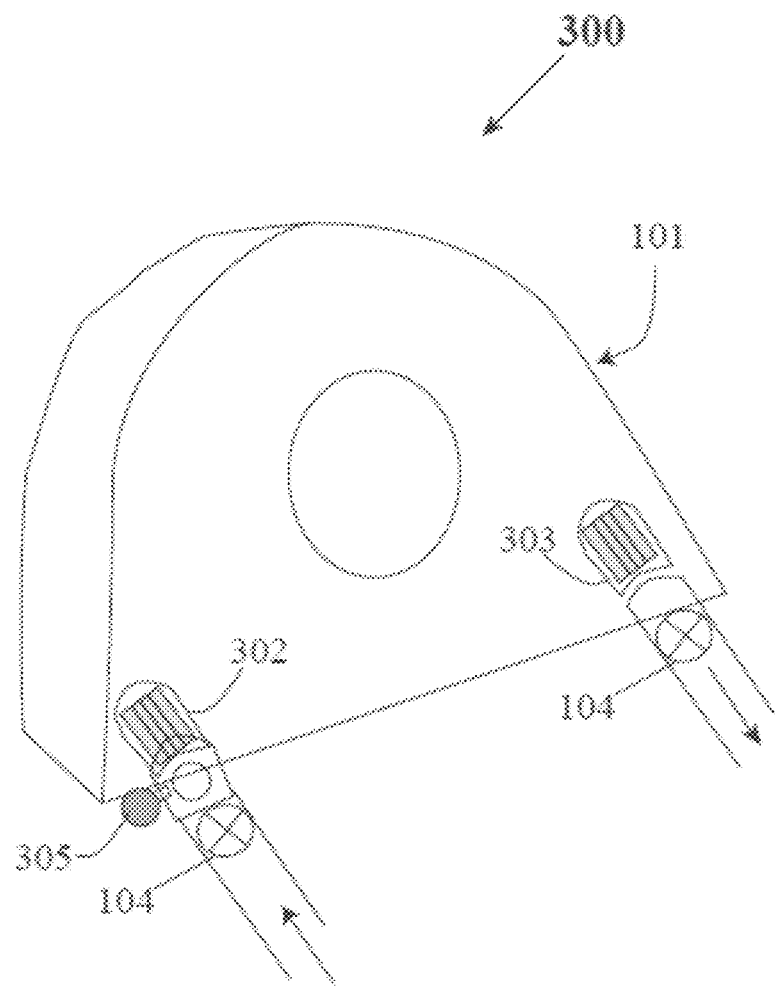
FIG. 3 illustrates details of an embodiment of the microprocessor-controlled blower with input port 202 and an output port, both provided with HEPA filters.
Figure 4:
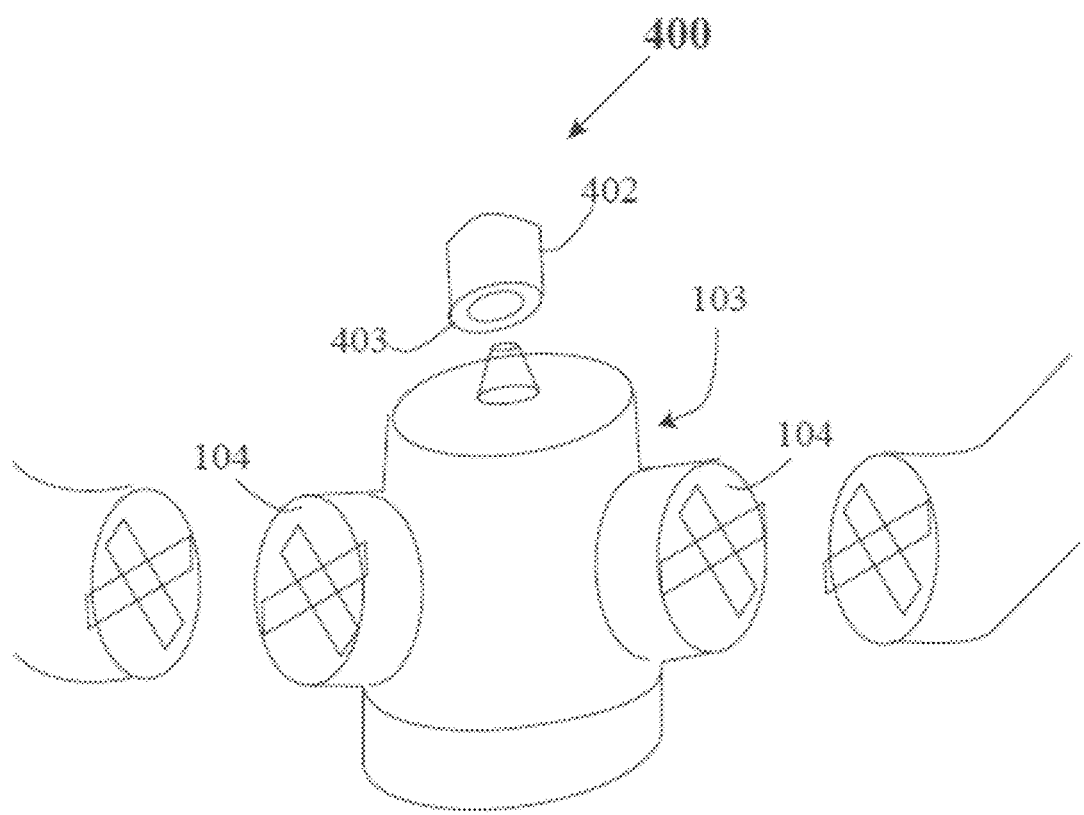
FIG. 4 illustrates an embodiment of the antimicrobial mist generator.
Figure 5:
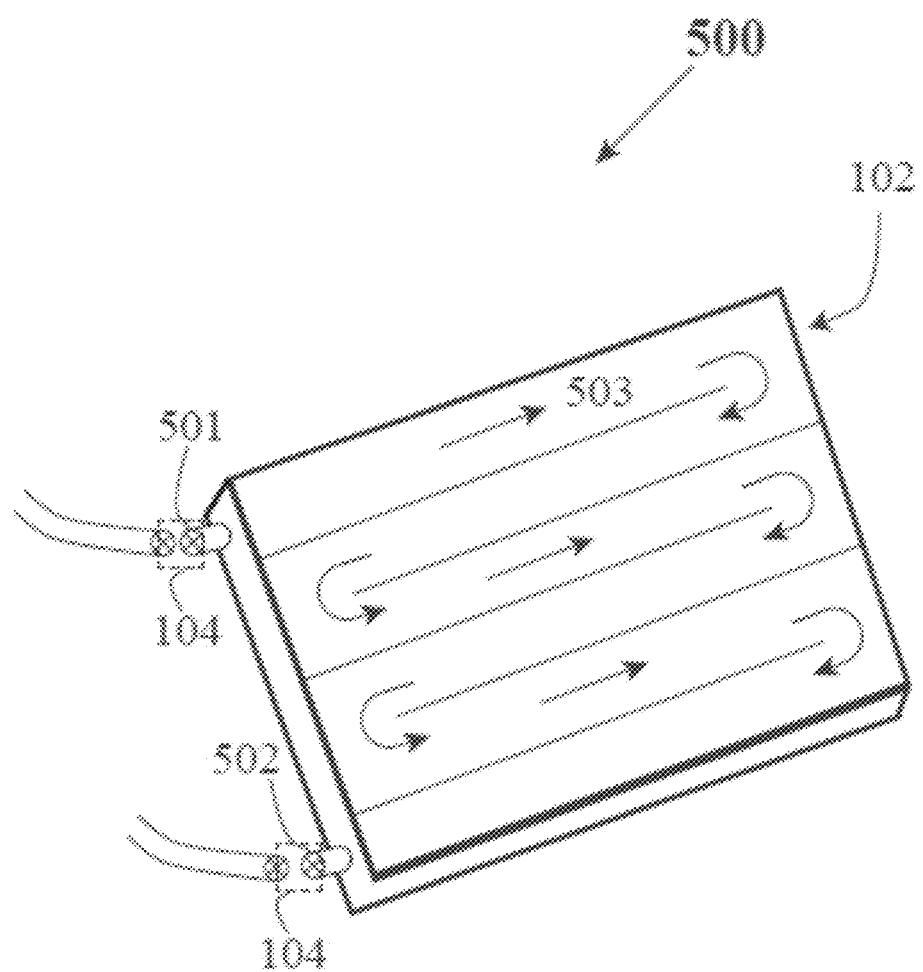
FIG. 5 illustrates an embodiment of the patient mattress or blanket.
Figure 6:
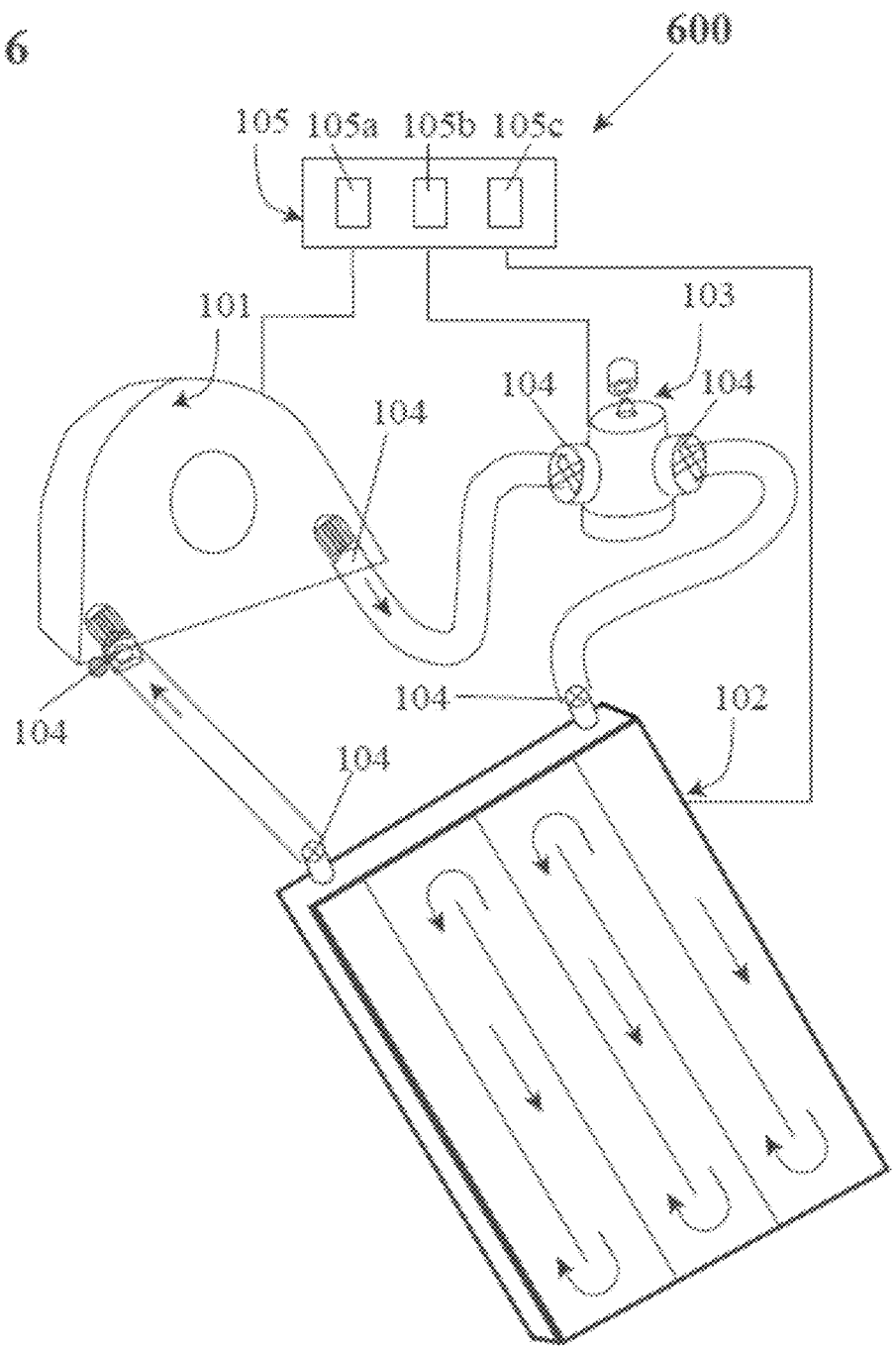
FIG. 6 illustrates an embodiment of the sterilization process of the patient bed or blanket prior to disposal.
Figure 7:
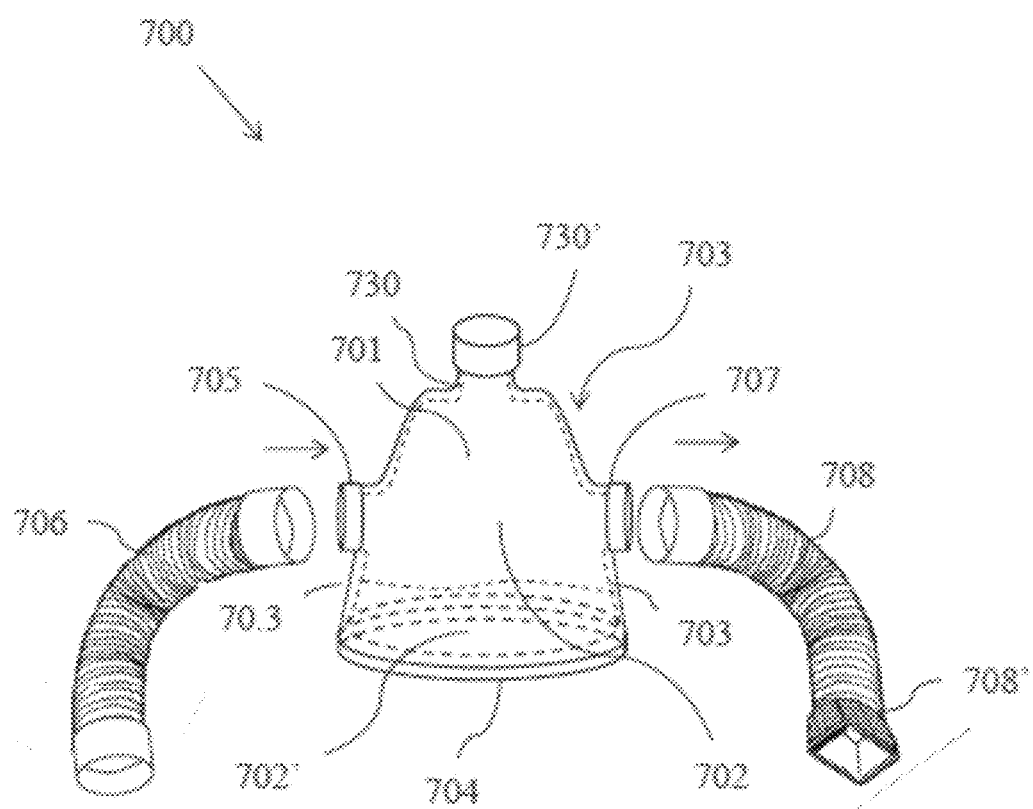
FIG. 7 illustrates another embodiment of the microprocessor-controlled antimicrobial mist generator.
Figure 8:
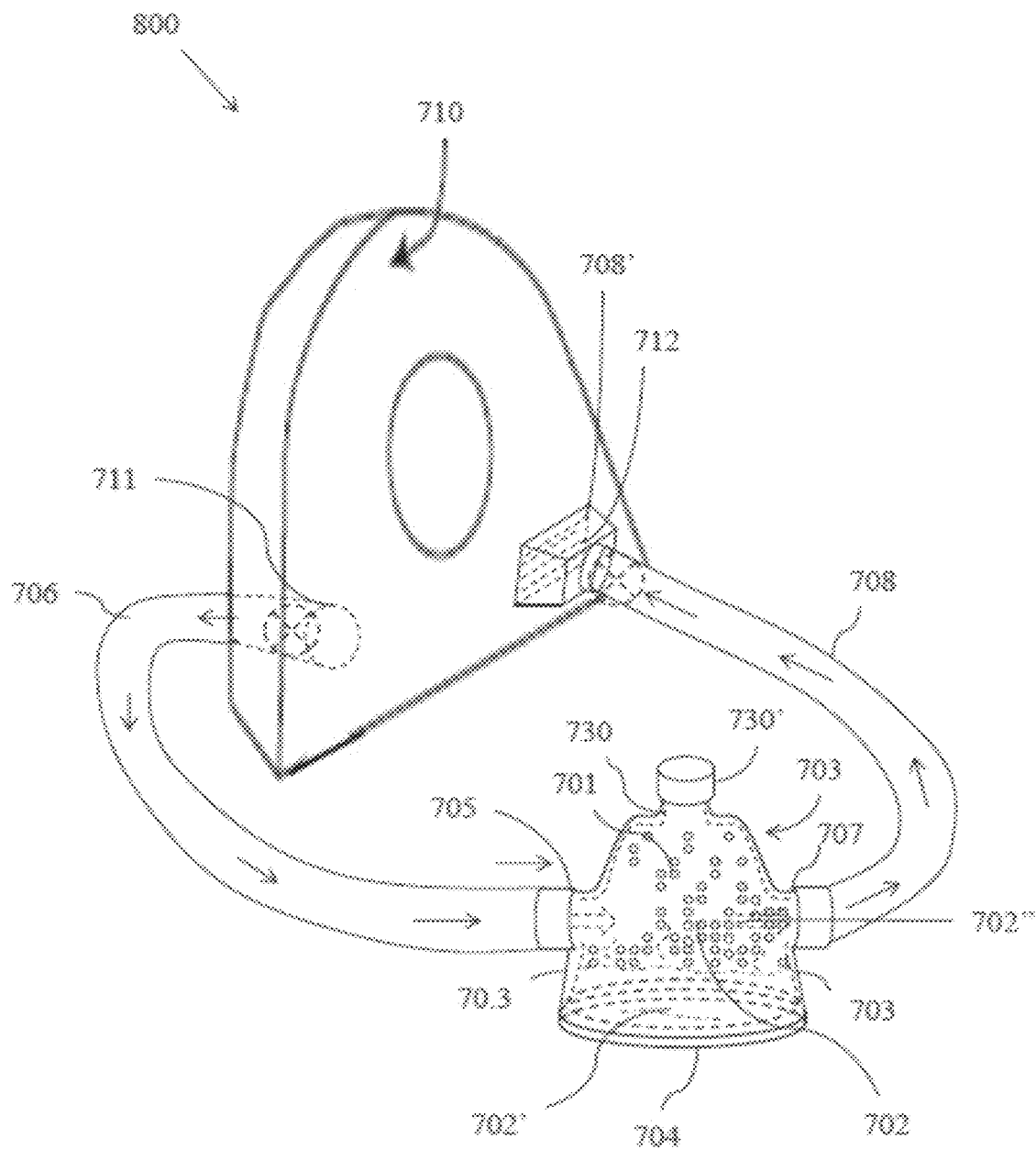
FIG. 8 illustrates the embodiment of FIG. 7 connected to a blower with air warmer machinery and flexible tubes being sterilized by the antimicrobial/disinfectant mist generator.

FIG. 2 illustrates at 200 the blower with air warmer machinery and flexible tubes used being sterilized by the antimicrobial mist generator. The blower with air warmer machinery is shown at 101 with HEPA filters both at inlet and outlet. The output of the blower is connected to the inlet of the antimicrobial mist generator 103 using a flexible hose provided with quick-release couplings. The output of the antimicrobial mist generator 103 is connected to the inlet port of the blower 101 using a flexible hose provided with quick-release couplings. The antimicrobial solution in the antimicrobial mist generator is atomized and circulated in this closed path for a preselected time period, which may be as long as 30 minutes, disinfecting the circuit sterilizing the blower with air warming machinery 101 and all the flexible hoses in the system. At the end of this disinfecting step, the quick release couplings are disconnected and reattached to the blower and the mat. Any moisture present in the blower 101 and flexible hoses can be blown into a dry sponge.

FIG. 3 illustrates at 300 the details of the microprocessor-controlled blower with warm air delivery 101. As illustrated, the blower has input port 302, and output port 303 both provided with HEPA filters in the illustration. The quick release connectors of the flexible hose are shown at 104. The warm air flow bath is indicated by the arrows. The blower with warm air delivery has a blower fan and electrical heating elements with sensors for air temperature, air pressure, and airflow rate communicating with the microprocessor control as shown in FIG. 1

FIG. 4 illustrates at 400 an embodiment of the antimicrobial mist generator, which is only used to achieve internal sterilization of the blower warm air machinery 101 and all the flexible hoses used. The mist generator is filled with a capsule 402 that has the antimicrobial liquid sealed with gasket 403, which is atomized by the flow of warm air through the input port and is delivered to the output port. In an alternative embodiment, a microprocessor may be provided, which preferably turns on the antimicrobial mist spray during initial set up to sterilize the interior surfaces of the blower and flexible tubes. When the sterilization operation is complete, an aliquot of sterile distilled water is introduced, and any residual disinfectant is vaporized in the circulated water vapor. Any remaining water can be taken up into a clean sponge or desiccant. Quick-release couplings 104 connect the flexible hoses to the inlet and outlet of antimicrobial mist generator 103. The mist generator is then disconnected from both flexible hoses and discarded.

FIG. 5 illustrates at 500 the patient bed or blanket 102 for a closed system. The inlet of warm air into the bed or blanket is shown at 501. The patient bed or blanket has a plurality of interconnected airflow paths indicated by arrows shown at 503. The outlet of the patient bed or blanket 102 is shown at

502. The connection of a flexible hose to the inlet and outlet is made using quick-release couplings 104.

FIG. 6 illustrates at 600 an optional arrangement for the sterilization process of the patient bed or blanket. This is similar to FIG. 1 except that the antimicrobial mist generator 103 is inserted between the blower warm air machinery 101 and the patient bed or blanket 102, and a closed circuit is formed using flexible hoses with quick release connectors 104. When used prior to disposal, the sterilization process can be run for about 15 minutes, and the sterilized patient bed or blanket is then discarded.

FIG. 7 illustrates another embodiment of the microprocessor-controlled antimicrobial mist generator, shown generally at 700. FIG. 8 illustrates the embodiment of FIG. 7 in-line with a non-closed circuit blower, shown generally at 800, forming a temporarily closed circuit.

Referring to FIGS. 7 and 8, the antimicrobial mist generator 703 is only used to achieve internal sterilization of the blower warm air machinery and all the flexible hoses associated therewith. The mist generator comprises a main body 701 having a top wall 730 with an opening 730' with a removable cap, the opening traversing into a chamber 702 adapted to receive a disinfectant shown generally at 702' (misting shown in FIG. 8 at 702"), side walls 703 and a bottom wall 704 that may include a bottom cover to allow access into the chamber of the main body for inserting and later removing desiccant and the like. The main body 701 further includes an inlet duct 705 adapted for attachment to a first hose 706 which, in turn, is adapted for attachment to an output opening 711 of a blower 710 for delivery of forced air into the chamber 702 to carry disinfectant misted air. The main body 701 also includes an output duct 707 adapted for attachment to a second hose 708 which in turn is adapted for attachment to a blower inlet 712 opening of the blower 710 for delivery of disinfectant misted air through internal components of the blower 710 to improve sterility of the blower 710 to mitigate microbial contamination of patient warmers and lifters and hospital environments when the blower is in use. Second hose 708 is attached to the blower inlet 712 by way of an attachment or modification to the inflow of the blower to accept that hose, shown generally at 708'. The blower with air warmer machinery is shown at 710 with HEPA filters at each inlet 712 and outlet 711.

The top wall opening 730' preferably includes a narrow (~5 cm) neck closed with a removable cap so that disinfectant, water, dry desiccant, etc., can be introduced through the neck/opening 730'. Owing to the narrow neck and opening 730', desiccant and other bulky solids cannot be easily removed, and therefore re-use is avoided. However, if the mist generator is not disposable, the bottom wall may include a bottom cap/base that is removable by screwing the same off to permit emptying of the mist generator.

Capsule or chamber 702 has the antimicrobial or disinfectant liquid sealed with a gasket/diaphragm, preferably at opening 730'. The liquid is atomized by the flow of warm air through the input port and is delivered to the output port. In an alternative embodiment, a transducer for misting the liquid may be provided. The antimicrobial mist generator may be microprocessor controlled wherein the controls turn on an antimicrobial mist spray during initial set up to sterilize the interior surfaces of blower air machinery and flexible tubes attached thereto. When the sterilization operation is complete, an aliquot of sterile distilled water is introduced, and any residual disinfectant is vaporized in the circulated water vapor. Any remaining water can be taken up into a clean sponge or desiccant. Quick-release couplings 104 connect the flexible hoses to the inlet and outlet of antimicrobial mist generator 103. The mist generator is then disconnected from both flexible hoses and discarded.

The antimicrobial mist generator is capable of being utilized as a stand-alone internal sterilizer for non-closed-circuit patient warmers. Antimicrobial mist generator includes a mist chamber for housing a disinfectant adapted to vaporize or form a mist upon contact with warm air. Preferably the outflow/outlet of the chamber is attached to flexible hose 704 connected to any non-closed circuit device, temporarily making it run as a closed circuit and allowing internal sterilization, including drying, without releasing the disinfectant vapor into the hospital environment. The generator, presumably, but not necessarily disposable, would achieve the internal sterilization that is currently impossible with the blower devices now in use.

Flexible hoses (fixed or detached) are attached to the mist generator via the inflow part of a warmer that is not closed circuit, creating a temporary closed circuit that allows internal sterilization. An aliquot of sterile water can be introduced after the sterilization takes place to remove residual disinfectant. A sponge or descant is inserted, and the system is again run to remove residual liquid/vapor.

FDA required "regular cleaning" of patient heating devices can be achieved with the subject system without changing any other components. Heated air takes up the fluid within the chamber whereupon it continues traveling with the warm forced air as a mist or vapor through tubes to sterilize devices attached thereto. Fluids contemplated include chemical compositions having relatively low boiling points or volatility so that the disinfectant vaporizes upon being heated by way of the warm air. Examples include alcohols such as ethanol etc.

FIG. 9*a* illustrates another embodiment of the antimicrobial mist generator, shown generally at 900. The antimicrobial mist generator 903 is generally used to achieve internal sterilization of the blower warm air machinery and all the flexible hoses used. The mist generator is filled with a capsule 902 that has the antimicrobial liquid sealed with gasket/diaphragm 905, which is atomized by the flow of warm air through the input port and is delivered to the output port. The antimicrobial mist generator 903 turns on the antimicrobial mist spray during initial set up to sterilize the interior surfaces of blower air machinery and flexible tubes attached thereto. When the sterilization operation is complete, an aliquot of sterile distilled water may be introduced, and any residual disinfectant is removed in the circulated water vapor. Quick-release couplings 904 connect the flexible hose to the inlet of antimicrobial mist generator 903. Antimicrobial mist generator 903 preferably includes an outlet 903' whereupon either a cap 906 or a quick release coupling 904 connecting to a flexible hose is preferably provided for connection of the mist generator 903 to patient warmer devices including for example blower warm air machinery (see FIGS. 2 and 10), or a mattress or a bed for sterilization thereof (see FIG. 6). The mist generator is disconnected from both flexible hoses after the system is dried internally by running the blower, and excess water is taken up into a clean sponge or desiccant.

The antimicrobial mist generator 903 is capable of being utilized as a stand-alone internal sterilizer for non-closed-circuit patient warmers (such as without limitation the kind use by 3M associated with the trade name BAIR and others). Antimicrobial mist generator 903 includes a mist chamber 910 for housing a disinfectant adapted to vaporize or form a mist upon contact with warm air. In this use, the outflow/outlet 903' of the chamber 910 is attached to flexible hose 904 connected to a non-closed circuit device, temporarily making it run as a closed circuit and allowing internal sterilization, including drying, without releasing the disinfectant vapor into the hospital environment (See FIG. 10). The generator, presumably, but not necessarily disposable, would achieve the internal sterilization that is currently impossible with the patient heating devices now in use. Preferably the mist generator 903 is shaped having a neck portion 921 at the top with a diameter substantially less than the diameter of a bottom portion 922. Preferably, neck portion 921 has a diameter of approximately 5 cm, which is substantially less than the diameter of a bottom portion 922 which, in turn, preferably includes curved walls so that the bottom portion is substantially bulbous. The bottom portion 922 may include a bottom opening with a removable bottom cover 923 that affords access to the chamber of the mist generator to allow addition and later removal of desiccant or fibers that can absorb circulating moisture, the cover 923 being necessary only if the mist generator is designed and employed for multiple use. The preferred embodiment is for the bottom portion to be solid, making it difficult to remove the solid desiccant that was easily introduced through the narrow neck of the upper portion 921, encouraging single-use and disposal of the used mist generator, thus avoiding the release of contaminated material and disinfectant into the hospital environment Flexible hoses (fixed or detached) from the outlet flow port of the mist generator to the inflow port of a blower that is a non-closed circuit, creating a temporary closed circuit that allows internal sterilization. An aliquot of sterile water can be introduced after the sterilization takes place to remove residual disinfectant, and then removed by uptake into a sponge or descant.

FDA recommended, "regular cleaning" of patient heating devices can be achieved with the subject system without changing any other components. Preferably to avoid a port into the chamber 910 that could be opened for filling, a soft diaphragm 905 is provided through which fluids can be introduced with a needle and syringe (similar to medicine vials). The disinfecting liquid may be contained in a sealed prefilled capsule, which is perforated when pushed into the chamber 910, releasing the enclosed fluid. The heated air causes the fluid of capsule 902 to atomize within chamber 910, whereupon it continues traveling with the warm forced air as a mist or vapor through tubes to sterilize devices attached thereto. Fluids contemplated include chemical compositions having relatively low boiling points or volatility so that the disinfectant vaporizes upon being heated by way of the warm air. Examples include alcohols such as ethanol etc. Embodiments of the capsule/cartridge are shown in FIGS. 9*b*-9*d*.

FIG. 9*b* illustrates another embodiment of a capsule/cartridge 950 adapted to be inserted within the mist generator of FIG. 9*a*. Capsule/cartridge 950 is a spray cartridge containing a liquid disinfectant/antimicrobial solution generally constructed as a spray bottle construction, including a reservoir 951 housing the liquid having a tube 952 therein. A cartridge pump 953 is provided with a trigger mechanism, a piston, a cylinder, and a one-way valve in-line with a spray nozzle 954. Spray nozzle 954 includes a one-way valve to prevent air from flowing back into the pump and allowing suction within the pump so that liquid is pulled through tube 952. Nozzle 954 concentrates the liquid into a stream forcing it through a small hole. When the trigger is pressed, it forces the piston into the cylinder, which forces the liquid through the nozzle as a concentrated stream of liquid. When the trigger is released, the piston moves back, pulling liquid back into the cylinder. This liquid is forced out of the nozzle the next time the trigger is pressed. A one-way valve at the bottom of the pump only allows liquid to flow up the tube into the pump, not back into the bottle. The mist generator preferably includes a spray activator herein shown as a bracket 955 that the capsule/cartridge 950 sits within when it is inserted in the chamber of the mist generator. Bracket 955 may be provided so that it is in-line with a manual button that, when depressed, presses the capsule/cartridge 950 downward and causes the trigger of the pump to be activated to release spray. Preferably, bracket 955 is in-line with an electronic switch that activates the trigger to cause release of the spray.

Figure 9A:
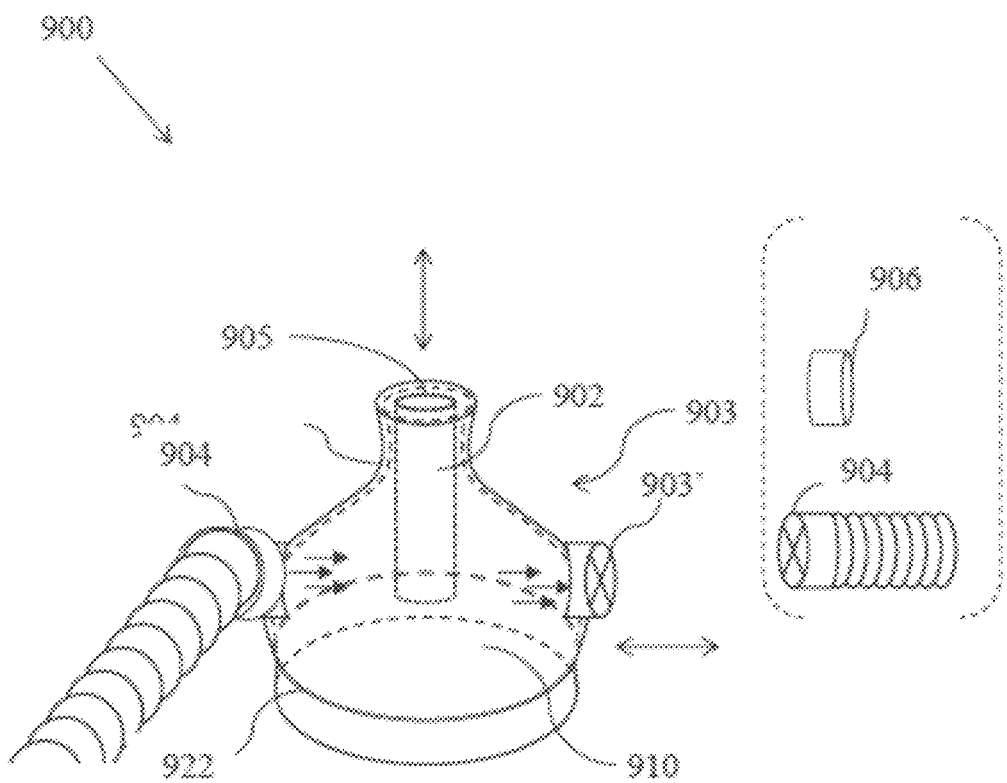
FIG. 9a illustrates another embodiment of the antimicrobial mist generator.
Figure 9B:
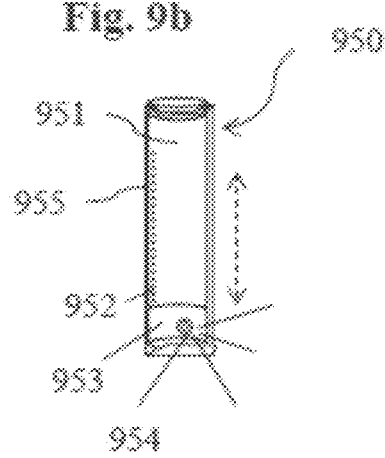
Figure 9C:
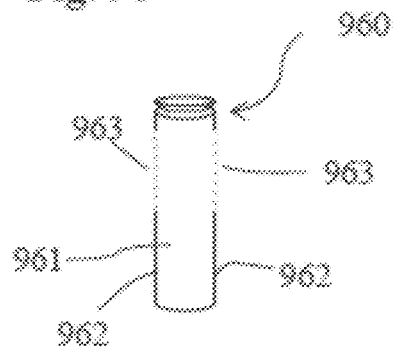
Figure 9D:
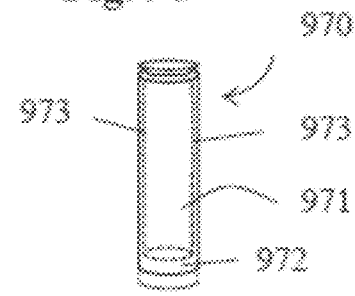
Figure 10:
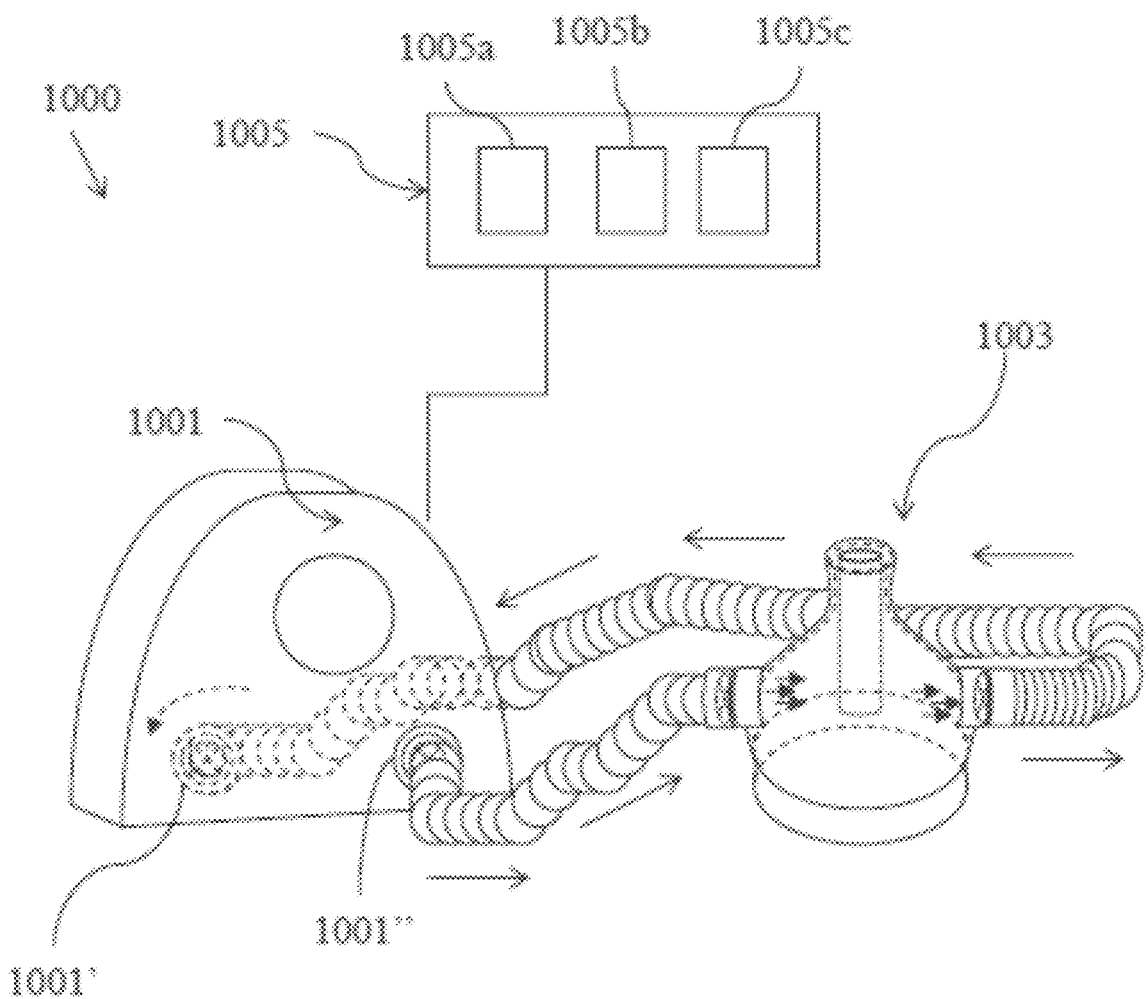
FIG. 10 illustrates the embodiment of FIG. 9 connected to a blower with air warmer machinery and flexible tubes being sterilized by the antimicrobial/disinfectant mist generator.
Figure 11:
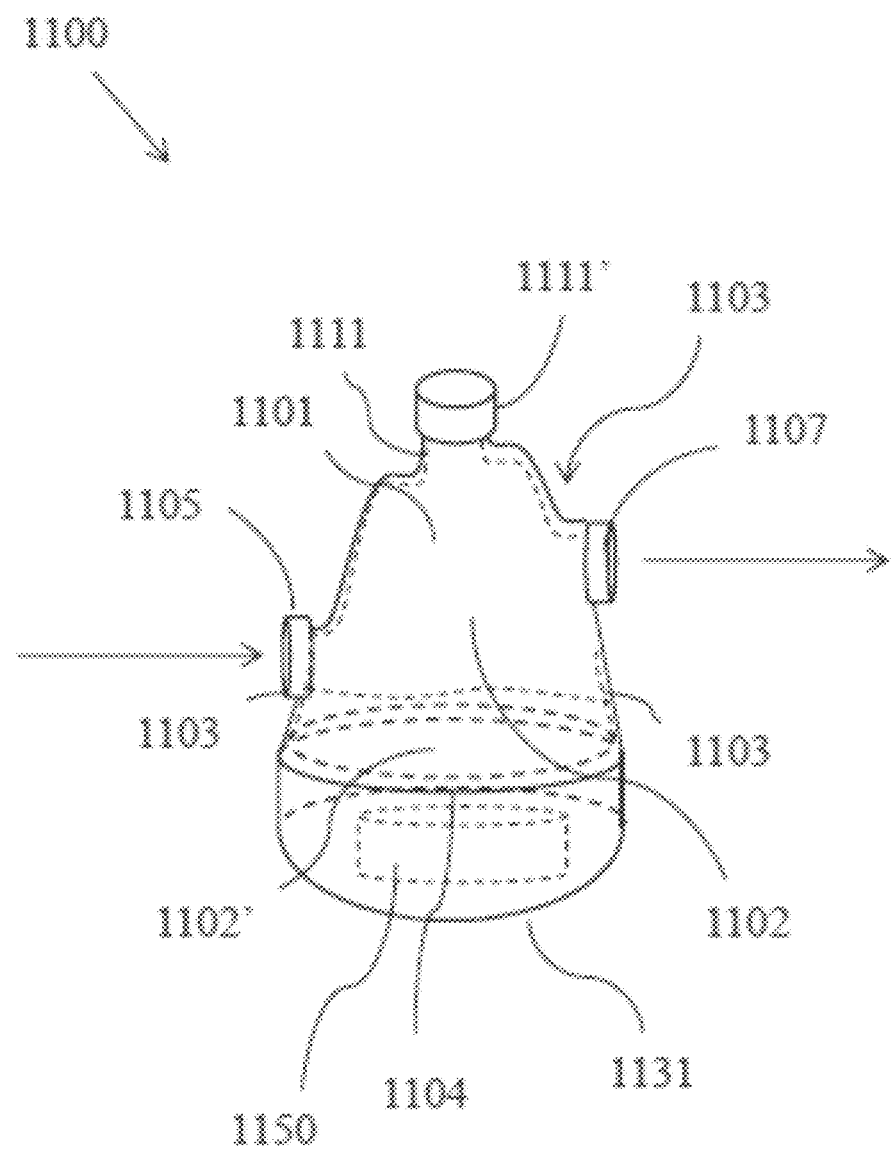
FIG. 11 illustrates another embodiment of the antimicrobial mist generator.
Figure 12A:
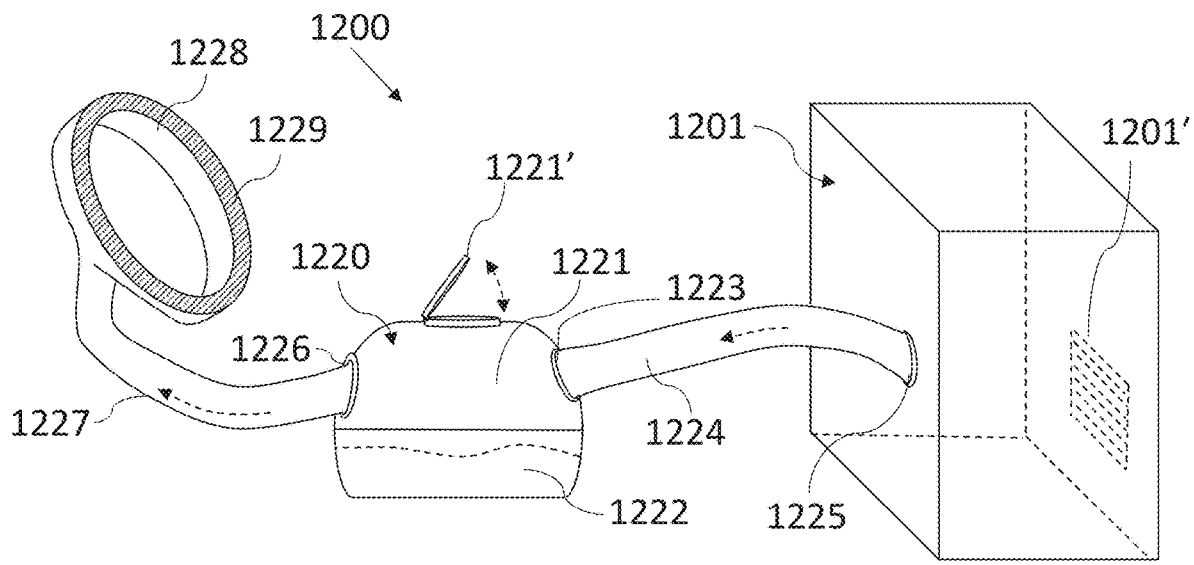
FIG. 12a illustrates another embodiment of the antimicrobial mist generator adapted for temporarily creating a closed circuit to sterilize internal structures with disinfectant vapor of a convective temperature management system used in a hospital or surgery center.
Figure 12B:
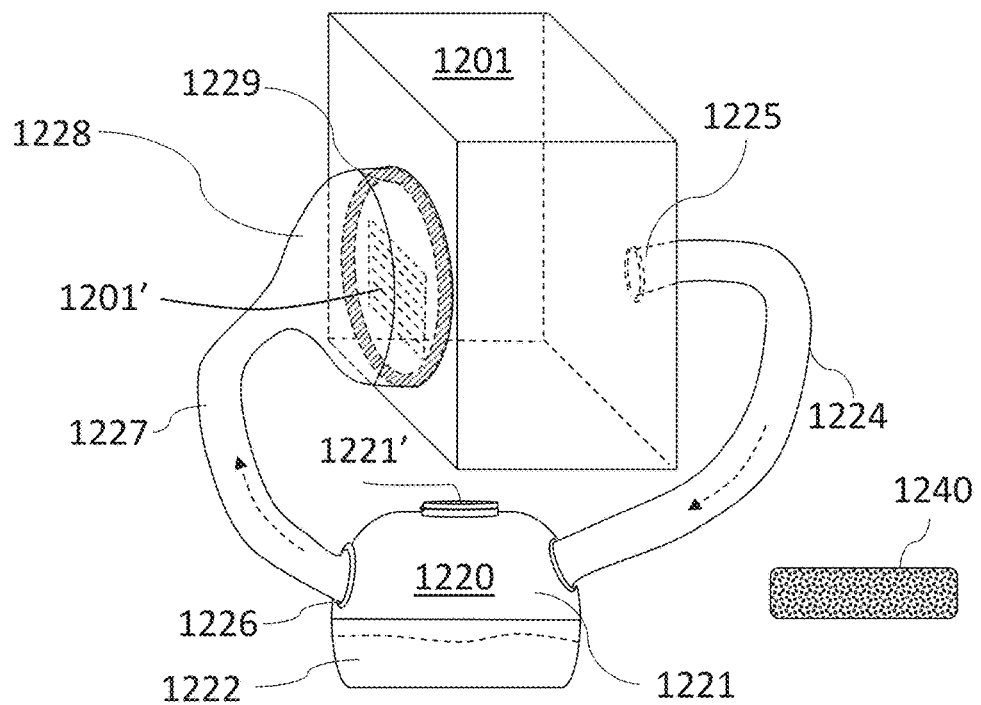
FIG. 12b illustrates the antimicrobial mist generator temporarily connected to the convective temperature management system.

FIG. 9*c* illustrates an embodiment of a capsule/cartridge 960 adapted to be inserted within the mist generator of FIG. 9*a*. In this embodiment, capsule/cartridge 960 includes a reservoir 961 holding a volatile disinfectant liquid and side walls 962 having at least a portion therein that include small apertures or perforations 963 for release of misted liquid as air passes through the chamber of the mist generator. It is noted that the reservoir 961 may hold a volatile disinfectant liquid, or a semi-solid or membrane holding the liquid that releases the liquid as forced heated air passes through the chamber of the mist generator.

A separate capsule/cartridge may be provided housing a fiber or desiccant when the mist generator is in a drying mode, such as after the disinfectant procedure is complete. The user simply places a capsule/cartridge housing the disinfectant into the chamber of the mist generator and runs a disinfectant operation for a period of time as shown in FIG. 10. When the disinfectant run is complete, the user can simply remove the capsule/cartridge and replace it with a drying capsule/cartridge that contains fiber or desiccant and performs a drying run for a period of time to dry liquid/residual mist from the generator, tubes, and blower. Upon completion, the capsules/cartridges, as well as the mist generator itself, are preferably discarded.

FIG. 9*d* illustrates another embodiment of a capsule/cartridge 970 adapted to be inserted within the mist generator of FIG. 9*a*. In this embodiment, the reservoir 971 housing the disinfectant is located within a capsule chamber 972. At least a portion of side walls 973 of the reservoir has apertures or holes therein for the escape of misted disinfectant as air passes through the chamber of the mist generator.

FIG. 10 illustrates at 1000 another embodiment of the blower with air warmer machinery and flexible tubes being sterilized by the antimicrobial mist generator. The blower with air warmer machinery is shown at 1001 with HEPA filters both at inlet and outlet 1001' and 1001". The output 1001" of the blower 1001 is connected to the inlet of the antimicrobial mist generator 1003 using a flexible hose provided with quick-release couplings. The output of the antimicrobial mist generator 1003 is connected to the inlet port 1001' of the blower 1001 using a flexible hose provided with quick release couplings temporarily forming a closed-circuit system. The antimicrobial solution in the antimicrobial mist generator is atomized and circulated in this closed path for a preselected time period, which may be as long as 15 minutes, disinfecting the circuit sterilizing the blower with air warming machinery 1001 and all the flexible hoses in the system. At the end of this disinfecting step, any moisture present in the blower 1001 and flexible hoses is taken up into a dry sponge. The quick-release couplings are then disconnected.

The microprocessor control panel is shown at 1005. The microprocessor controls the warm air temperature at 1005*a* warm airflow rate at 1005*b* and warm air pressure at 1005*c*. The warm airflow path is, therefore, a continuous closed circuit with no warm air escape location. The airflow rate is proportional to the speed of rotation of the blower motor. The electrical current supplied to the heating elements controls the warm air temperature.

FIG. 11 illustrates another embodiment of the subject mist generator, shown generally at 1100. The mist generator comprises a main body 1101 having a top wall 1111 with an opening 1111', the opening traversing into a chamber 1102 adapted to receive a disinfectant shown generally at 1102', side walls 1103 and a bottom wall 1104. The main body 1101 further includes an inlet duct 1105 adapted for attachment to a first hose which in turn is adapted for attachment to an output opening of a blower for delivery of forced air into the chamber 1102 to create misted disinfectant in the air. The main body 1101 also includes an output duct 1107 adapted for attachment to a second hose, which in turn is adapted for attachment to a blower inlet opening of the blower for delivery of disinfectant misted air through internal components of the blower. In the embodiment shown, the bottom wall 1104 includes a bottom opening with a removable bottom cover 1131, which can cause the removal of the main body 1101 from bottom cover 1131 for insertion of desiccant, and/or paper towels, etc. In the embodiment shown, cover 1131 also includes an optional transducer 1150 for vibration misting the liquid within the chamber.

FIGS. 12*a*-12*b* illustrate an embodiment of the antimicrobial mist generator for temporarily creating a closed circuit to sterilize internal structures with disinfectant vapor for a convective temperature management system used in a hospital or surgery center. FIG. 12*a* illustrates the antimicrobial mist generator appointed for attachment to the temperature management system, shown generally at 1200. FIG. 12*b* illustrates the antimicrobial mist generator temporarily attached to the antimicrobial mist generator for sanitization. The convective temperature management system is appointed to be used in a hospital or surgery center to maintain a patient's core body temperature, such as that referred to as the Bair Hugger by 3M.

The system generally consists of a reusable warming unit or blower 1201 and a single-use disposable warming blankets for use before, during, and after surgery. A mist generator for improved sterility of blowers having controlled forced air delivery is shown at 1220 having a top wall with an opening having a cap 1221' that traverses into a chamber 1221. Chamber 1221 is adapted to receive a liquid disinfectant/antibacterial solution and/or water shown generally at 1222 inserted into chamber 1221. Alternatively, disinfectant/antibacterial solution and/or water is absorbed in a sponge or porous surface wherein the disinfectant/antibacterial solution and/or water is absorbed that is appointed to be placed within chamber 1221. An inlet duct 1223 is integrated in chamber 1221, which is adapted for attachment to a first hose 1224 which, in turn, is adapted for attachment to an output opening 1225 of the blower 1201 for delivery of forced air into the chamber 1221 to carry disinfectant misted air. Chamber 1221 includes an output duct 1226 adapted for attachment to a second hose 1227 which, in turn, is adapted for attachment to a blower inlet opening 1201' of the blower 1201 for delivery of disinfectant misted air through internal components of the blower 1201 so that the mist generator improves sterility of the blower 1201 to mitigate microbial contamination of patient warmers and lifters and hospital environments. A closed-circuit is temporarily created to sterilize the internal structures of the otherwise open circuit heating device of the blower 1201 with disinfectant vapor.

Second hose 1227 includes an attachment end 1228 formed to substantially completely cover and substantially seal over the blower inlet opening 1201' of blower 1201. Preferably, attachment end 1228 is constructed having a substantially flat rim 1229 with an adhesive surface 1230 for adhering attachment end 1228 against blower 1201 sealing around blower inlet opening 1201'. A seal or gasket may be integrated circumferentially around the entire rim 1229 for forming a substantially water-tight seal. After sterilization is complete and the liquid dry, a dry desiccant 1240 is appointed to be inserted into the chamber 1221 to dry the internal components of the blower 1201, hoses, and mister.

Figure 13:
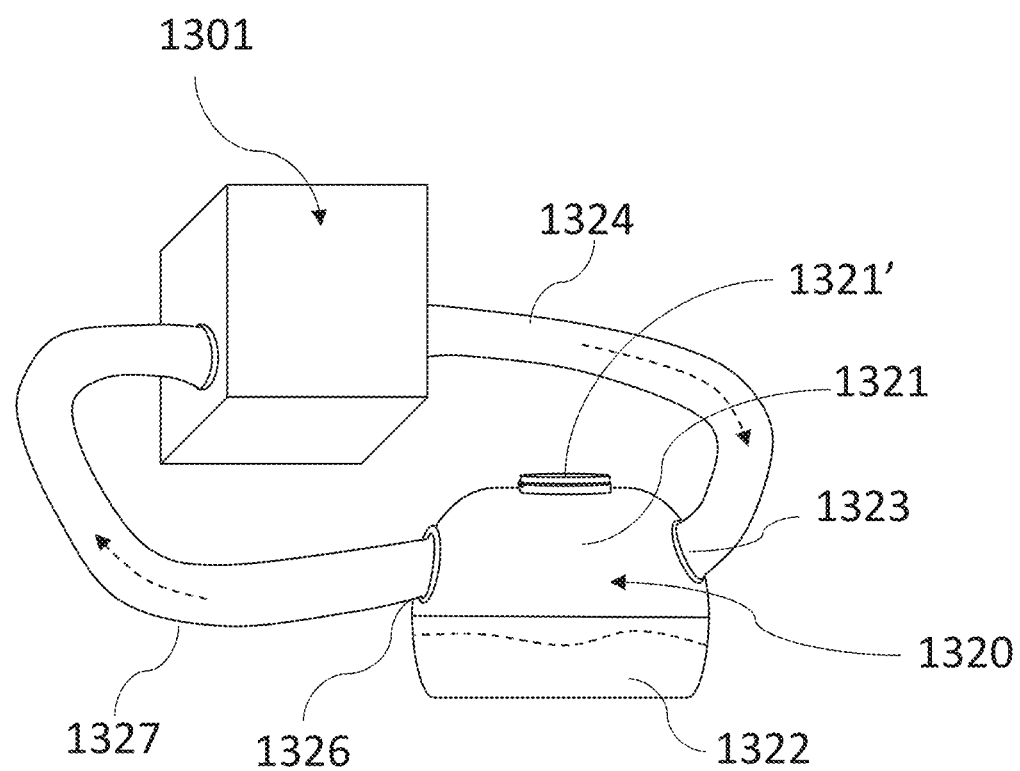
FIG. 13 illustrates an embodiment of the antimicrobial mist generator temporarily attached to a hospital ventilator, anesthesia machine, or oxygen support system.

FIG. 13 illustrates an embodiment of an antimicrobial mist generator 1320 temporarily attached to a blower 1301 of a hospital ventilator, anesthesia machine, or oxygen support system. Mist generator 1320 has a top wall with an opening with lid/cap 1321' that traverses into a chamber 1321 that receives a disinfectant/antibacterial solution and/or water shown generally at 1322. Chamber 1321 has an inlet duct 1323 attached to a first hose 1324 attached to an output opening 1325 of the blower 1301 for delivery of forced air into the chamber 1321 to carry disinfectant misted air. Chamber 1321 includes an output duct 1326 adapted for attachment to a second hose 1327 which, in turn, is adapted for attachment to a blower inlet opening of the blower 1301. Second hose 1327 includes an attachment end formed to substantially completely cover and substantially seal over the blower inlet opening of blower 1301. After sterilization is complete and the liquid dry, a dry desiccant is appointed to be inserted into the chamber 1321 to dry the internal components of the blower 1301, hoses, and mister. The chamber, liquid and/or desiccant can all be single-use and/or disposable.

Figure 14A:
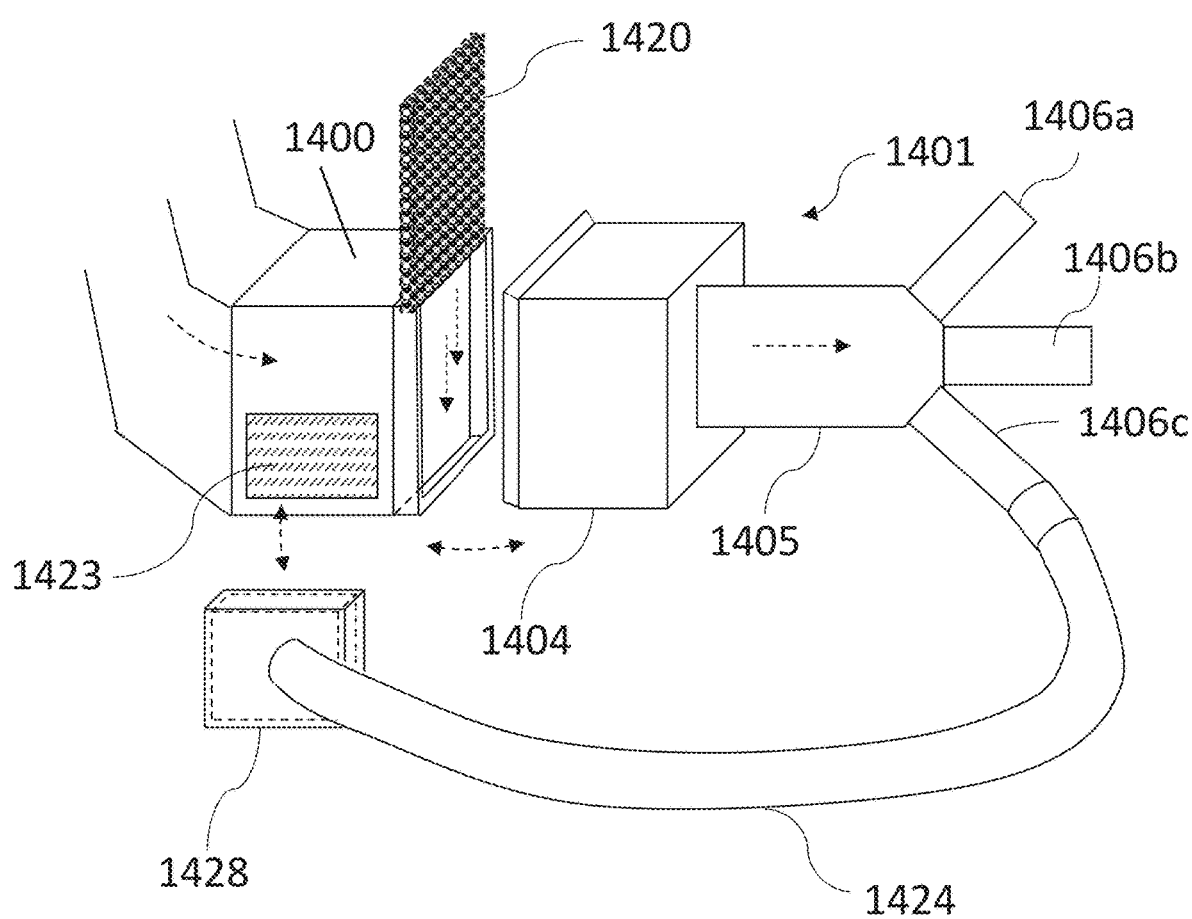
FIG. 14a illustrates another embodiment of the antimicrobial mist generator in which a closed circuit is temporarily created to sterilize internal structures with the disinfectant vapor of a heating/cooling/air circulation device.
Figure 14B:
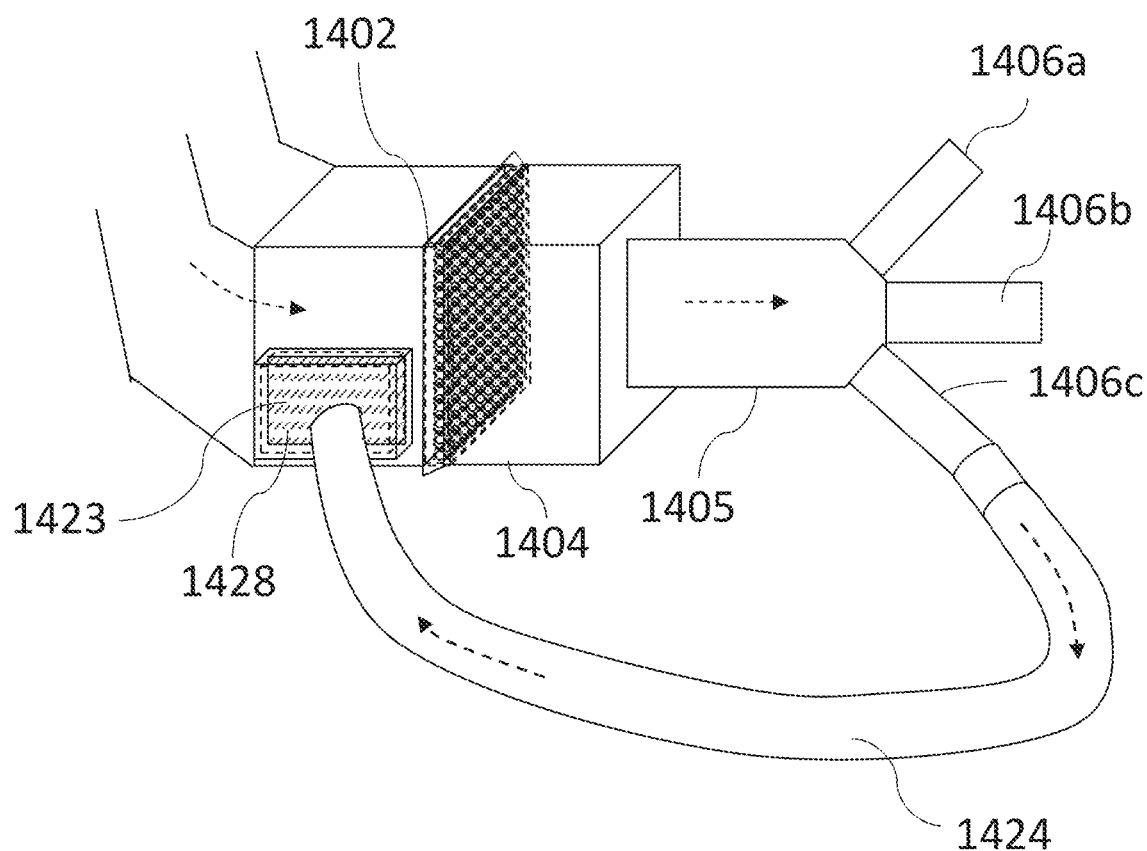
FIG. 14b illustrates a top plan view wherein the sterilizing grid is inserted in the system and the system is configured in a closed circulating circuit for sterilization.

FIG. 14a illustrates another embodiment of the antimicrobial mist generator in which a closed circuit is temporarily created to sterilize internal structures with the disinfectant vapor of a heating/cooling/air circulation device. FIG. 14b illustrates a top plan view wherein the disposable filter/sponge, which becomes a sterilizing grid, is inserted into the slot normally occupied by the dry dust filter and the system is temporarily configured into a closed circulating circuit for sterilization. Disposable filter/sponge 1420 is sized and shaped to fit into the system's filter slot or filter port 1402.

System 1401 includes a chamber 1400 removably connected to an air handler 1404 connected to a main vent 1405, in turn, feeding to vents 1406a, 1406b, and 1406c. All but one outlet/vent is closed, herein vents 1406b and 1406c are closed, and vent 1406a remains open and is connected by a hose 1424 with an attachment end 1428 formed to substantially completely cover and substantially seal over a return duct 1423 of chamber 1400 of system 1401 (see FIG. 14b). When the hose 1424 attachment end 1428 is placed over return duct 1423 and the disposable filter/sponge inserted in to the filter slot of chamber 1400 the closed system is then run.

Disinfectant filter/sponge 1420 is formed as a sterilizing grid with a screen or pores more open than a standard filter coated with a soft porous surface material that holds liquid disinfectant or water. Alternatively, filter/sponge may be dry and/or impregnated prior to insertion. Air flowing through will take up and distribute disinfectant to internal surfaces of the system and sterilize them. After grid/disinfectant filter/sponge 1420 is dry, it is removed, and the same filter/sponge or grid is impregnated, or another is inserted, and water is taken up by flowing air and distributed throughout the system. Additional water may be added, and disinfectant is taken up in the water. The grid/filter/sponge 1420 is removed and another grid, composed, covered or filled with a desiccant material is inserted. As moving air carries internal moisture to the desiccant here, it is absorbed. The grid/filter/sponge 1420 is then removed and discarded and the standard dust filter reinserted in the system. The internal portion of the system is now sterilized, and the circulating air is free of any disinfectant.

To establish a closed system, vents 1406a and 1406b must be covered and closed during operation. The circulating air returns to the system via a return vent 1423. Any additional return vents must be occluded, either by an adhesive plastic wrap (i.e., such as that sold under the name saran wrap) or by some other cover or wrap 1428, which may have adhesive edges for fixation. Airflow within the system requires an outlet to be left open, and a conduit 1420 from the open outlet to the return vent 1423 or central return duct 1400 The conduit may be disposable, attaching temporarily at both the outlets and over the return, or installed permanently, in which case an internal shut off within the conduit 1424 may be required.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A mist generator for improved sterility of blowers having controlled forced air delivery, consisting of:
   a) a main body having a top wall with an opening, the opening traversing into a chamber adapted to receive a disinfectant, side walls, and a bottom wall, said disinfectant comprising an alcohol-based solution containing at least one of isopropyl alcohol, ethanol, and n-propanol solutions containing 60% to 95% alcohol, or a non-alcohol based solutions containing benzalkonium chloride or triclosan, or an aqueous solution having an alcohol solution or an antiseptic therein;
   b) an inlet duct or aperture adapted for attachment to a first hose which in turn is adapted for attachment to an output opening of a blower for delivery of forced air into the chamber to carry disinfectant misted air;
   c) an output duct or aperture adapted for attachment to a second hose which in turn is adapted for attachment to a blower inlet opening of the blower for delivery of disinfectant misted air through internal components of the blower;
   whereby the mist generator improves sterility of the blower to mitigate microbial contamination of forced air delivery systems.

2. The mist generator as recited by claim 1, wherein the blower is part of a closed circuit.

3. The mist generator as recited by claim 1, wherein the blower having controlled forced air delivery is a commercial or residential heating or cooling system.

4. The mist generator as recited by claim 1, wherein said blower having controlled forced air delivery is a ventilator or respirator.

5. The mist generator as recited by claim 1, wherein said blower having controlled forced air delivery is an anesthesia device.

6. The mist generator as recited by claim 1, wherein said blower has microprocessor-controlled air heating capability for delivery of heated forced air, and said disinfectant is adapted to evaporate due to the heated forced air to yield misted air containing disinfectant.

7. The mist generator as recited by claim 6, wherein said disinfectant is a volatile liquid component that is adapted to vaporize as forced air blows over said disinfectant.

8. The mist generator as recited by claim 6, wherein said disinfectant is a volatile liquid component saturated within a substrate and said liquid vaporizes and escapes said substrate as forced air blows over said substrate.

9. The mist generator as recited by claim 1, wherein said mist generator is disposable.

10. The mist generator, as recited by claim 1, wherein said disinfectant is contained in a capsule adapted to be inserted within said chamber of said mist generator.

11. A mist generator for improved sterility of blowers having controlled forced air delivery, consisting of a disinfectant filter formed as a sterilizing grid having a screen coated with a soft porous surface material impregnated with a liquid disinfectant, said disinfectant comprising an alcohol-based solution containing at least one of isopropyl alcohol, ethanol, and n-propanol solutions containing 60% to 95% alcohol, or a non-alcohol based solution containing benzalkonium chloride or triclosan, or an aqueous solution having an alcohol solution or an antiseptic therein, wherein said soft porous surface material releases or dissolves to release said liquid disinfectant, whereby the mist generator improves sterility of a blower to mitigate microbial contamination of forced air delivery systems.

12. The mist generator as recited by claim 11, wherein said blower is part of a closed circuit.

13. The mist generator as recited by claim 11, wherein said blower having controlled forced air delivery is a commercial or residential heating or cooling system and wherein said disinfectant filter is adapted to be temporarily fitted in said commercial or residential heating or cooling system.

* * * * *